United States Patent
Sato et al.

(10) Patent No.: US 8,197,484 B2
(45) Date of Patent: Jun. 12, 2012

(54) ASSEMBLY FOR MINIMALLY INVASIVE REDUCTION OF HIP FRACTURE

(75) Inventors: Takashi Sato, Niigata (JP); Andrew H. Berthusen, Leesburg, IN (US); Derek C. Finch, Warsaw, IN (US); Bryan C. Mendenhall, Claypool, IN (US)

(73) Assignee: DePuy Products, Inc., Warsaw, IN (US)

( * ) Notice: Subject to any disclaimer, the term of this patent is extended or adjusted under 35 U.S.C. 154(b) by 932 days.

(21) Appl. No.: 11/789,332

(22) Filed: Apr. 24, 2007

(65) Prior Publication Data
US 2008/0275447 A1 Nov. 6, 2008

(51) Int. Cl.
*A61B 17/68* (2006.01)
(52) U.S. Cl. .......... 606/86 B; 606/89; 606/99; 606/104; 606/915
(58) Field of Classification Search ............... 606/86 A, 606/86 B, 96, 914, 915, 99, 281, 97, 98, 103, 606/104, 105, 105.5, 279
See application file for complete search history.

(56) References Cited

U.S. PATENT DOCUMENTS

| | | | |
|---|---|---|---|
| 2,526,959 A | | 10/1950 | Lorenzo |
| 3,554,193 A | | 1/1971 | Konstantinou et al. |
| 3,945,377 A | * | 3/1976 | Kronner ........................ 606/96 |
| 4,009,712 A | | 3/1977 | Burstein et al. |
| 4,438,762 A | | 3/1984 | Kyle |
| 4,465,065 A | | 8/1984 | Gotfried |
| 5,116,338 A | * | 5/1992 | Poggie et al. ................... 606/90 |
| 6,663,638 B2 | * | 12/2003 | Ralph et al. ...................... 606/99 |
| 7,481,813 B1 | * | 1/2009 | Purcell ....................... 606/86 R |

(Continued)

FOREIGN PATENT DOCUMENTS
EP 1574175 A1 * 9/2005
(Continued)

OTHER PUBLICATIONS

DePuy Orthopaedics' brochure entitled "Captured Hip Screw System Surgical Technique"; Published at least as early as Apr. 23, 2006; nineteen (19) pages.
(Continued)

*Primary Examiner* — Eduardo C Robert
*Assistant Examiner* — Jerry Cumberledge
(74) *Attorney, Agent, or Firm* — Maginot, Moore & Beck

(57) ABSTRACT

An assembly includes a holder having a first arm and a second arm, the holder being movable between a first configuration and a second configuration. The assembly further includes an actuator movable in relation to the holder between a first position and a second position. Movement of the actuator from the first position to the second position causes movement of the holder from the first configuration to the second configuration. The first arm has a first bone plate contact portion, and the second arm has a second bone plate contact portion. The first bone plate contact portion and the second bone plate contact portion are separated by a first distance when the holder is in the first configuration. The first bone plate contact portion and the second bone plate contact portion are separated by a second distance when the holder is in the second configuration. The first distance is greater than the second distance. The assembly further includes a bone plate having a plurality of fastener openings defined therein. The holder retains the bone plate between the first bone plate contact portion of the first arm and second bone plate contact portion of the second arm when the holder is positioned in the second configuration.

38 Claims, 25 Drawing Sheets

U.S. PATENT DOCUMENTS

| | | |
|---|---|---|
| 2003/0009168 A1* | 1/2003 | Beale et al. ................. 606/61 |
| 2003/0040752 A1* | 2/2003 | Kitchens ..................... 606/86 |
| 2004/0147937 A1* | 7/2004 | Dunbar et al. .............. 606/99 |
| 2004/0260289 A1 | 12/2004 | Padget et al. |
| 2005/0027293 A1* | 2/2005 | LeHuec et al. .............. 606/61 |
| 2005/0038444 A1 | 2/2005 | Binder, Jr. et al. |
| 2005/0049594 A1* | 3/2005 | Wack et al. ................. 606/69 |
| 2006/0074418 A1* | 4/2006 | Jackson ....................... 606/61 |
| 2006/0079909 A1* | 4/2006 | Runco et al. ................ 606/99 |
| 2006/0293690 A1* | 12/2006 | Abdelgany ................. 606/103 |
| 2007/0213726 A1* | 9/2007 | McGarity et al. ........... 606/69 |

FOREIGN PATENT DOCUMENTS

| | | |
|---|---|---|
| WO | 2003015650 | 2/2003 |
| WO | 2007092441 | 8/2007 |

OTHER PUBLICATIONS

European search report in a corresponding European application (i.e. EP 08 25 1504), 3 pages.

* cited by examiner

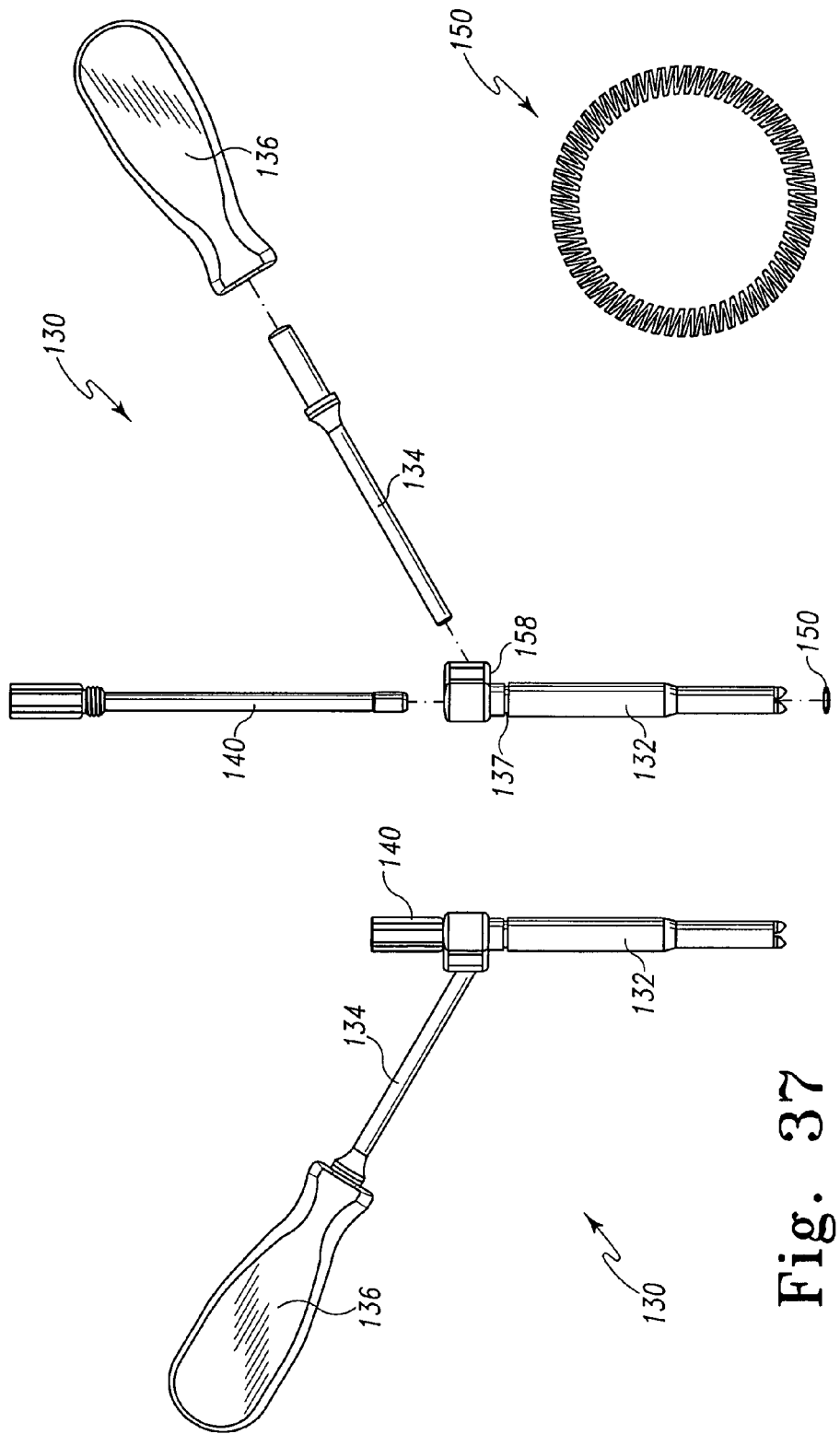

US 8,197,484 B2

ASSEMBLY FOR MINIMALLY INVASIVE REDUCTION OF HIP FRACTURE

BACKGROUND

The present disclosure relates generally to the reduction of a hip fracture by the placement of a bone plate and associated bone fasteners with instrumentation in a minimally invasive manner.

A procedure regularly performed by orthopaedic surgeons is the reduction of a hip fracture caused by trauma. The site of this type of fracture typically exists at the proximal portion of the femur below the head. In order to reduce a fracture of this type, an elongated lag screw is threadingly advanced into the shaft, neck, and head of the femur, and secured to a bone plate. Cortical screws are used to secure the bone plate to the femur distal to the fracture site. Tightening of the lag screw compresses the bone fragments together and facilitates healing of the femur. Many devices have been designed for this type of reduction including the devices disclosed in U.S. Pat. Nos. 4,438,762, 3,554,193, and 2,526,959, the disclosures of which are incorporated herein by reference in their entirety.

The above described devices are intended to be implanted by conventional or opening surgical techniques. Although conventional implantation of a bone plate of the type described above is an accepted procedure, it presents some disadvantages. In particular, a relatively large incision must be created in the leg to obtain access to the fracture site. The large incision may result in substantial soft tissue damage that requires a relatively long healing time thereby resulting in longer hospitalization due to post operative recovery. Moreover, the relatively large incision made during the above surgical procedure may cause a significant amount of unattractive scarring.

What is needed therefore is an assembly that is utilized by a surgeon to achieve reduction of a hip fracture through a relatively small incision. What is also needed is an assembly that is utilized by a surgeon to achieve reduction of a hip fracture with less damage to soft tissue. What is further needed is an assembly that is utilized by a surgeon to achieve reduction of a hip fracture that results in less scarring to a patient.

SUMMARY

In accordance with one embodiment of the disclosure, there is provided an assembly that includes a holder having a first arm and a second arm, the holder being movable between a first configuration and a second configuration. The assembly further includes an actuator movable in relation to the holder between a first position and a second position, wherein movement of the actuator from the first position to the second position causes movement of the holder from the first configuration to the second configuration. In addition, the assembly includes a bone plate having a plurality of fastener openings defined therein, the bone plate being retained between the first arm and the second arm when the holder is positioned in the second configuration.

Pursuant to another embodiment of the disclosure, there is provided an assembly that includes a holder having a first arm and a second arm, the holder being movable between a first configuration and a second configuration. The assembly further includes an actuator movable in relation to the holder between a first position and a second position. Movement of the actuator from the first position to the second position causes movement of the holder from the first configuration to the second configuration. The first arm has a first bone plate contact portion, and the second arm has a second bone plate contact portion. The first bone plate contact portion and the second bone plate contact portion are separated by a first distance when the holder is in the first configuration. The first bone plate contact portion and the second bone plate contact portion are separated by a second distance when the holder is in the second configuration. The first distance is greater than the second distance.

BRIEF DESCRIPTION OF THE DRAWINGS

FIG. 37 is a side elevational view of the subassembly of the drill guide assembly shown in FIG. 36;

FIG. 38 is an exploded, side elevational view of the subassembly of the drill guide assembly shown in FIG. 37;

FIG. 39 is a side elevational view of the ring of the subassembly of the drill guide assembly shown in FIG. 36;

DESCRIPTION OF THE PREFERRED EMBODIMENTS

Figure 1:
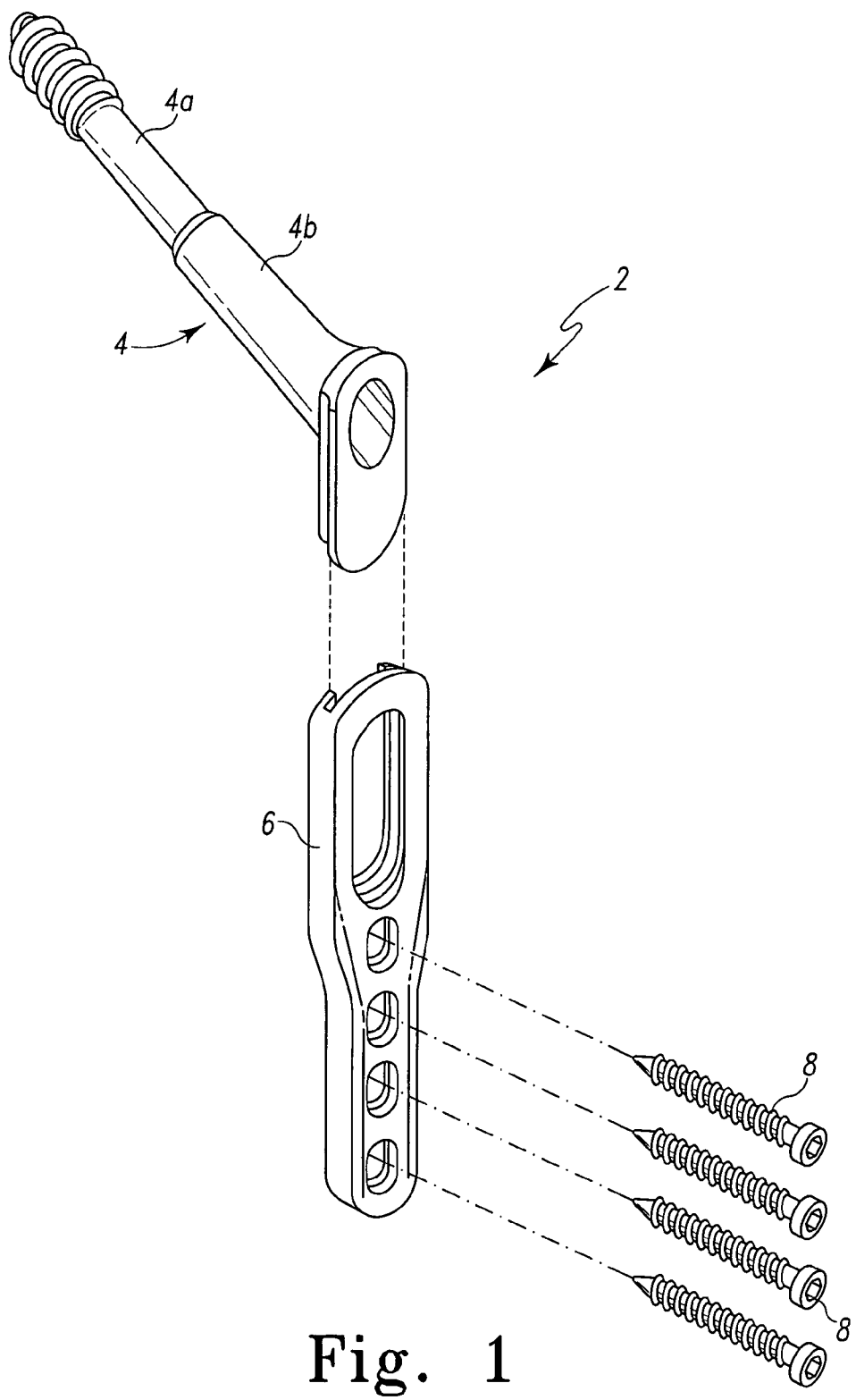
FIG. 1 is an exploded, perspective view of an implant assembly implanted which is implanted in a minimally invasive manner according to the present disclosure.
Figure 2:
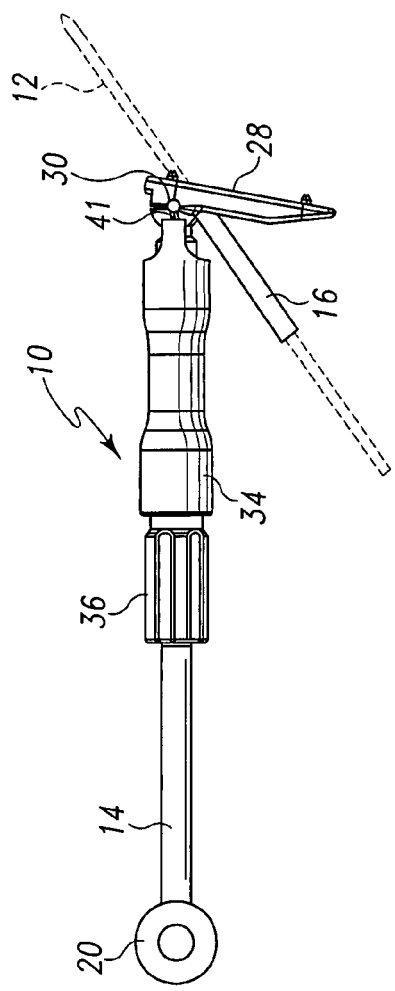
FIG. 2 is a side elevational view of a guide assembly that is used in the implantation of the implant assembly of FIG. 1 according to the present disclosure.

While the assembly described herein is susceptible to various modifications and alternative forms, specific embodiments thereof have been shown by way of example in the drawings and will herein be described in detail. It should be understood, however, that there is no intent to limit the assembly to the particular forms disclosed, but on the contrary, the intention is to cover all modifications, equivalents, and alternatives falling within the spirit and scope of the invention as defined by the appended claims.

Instrumentation and Implant Components

Described below are instrumentation and implant components that facilitate reduction of a hip fracture in a minimally invasive manner. The implant components comprise an implant assembly 2 that includes a captured screw assembly 4, a side plate 6, and a plurality of bone screws 8 as shown in FIG. 1. The captured screw assembly 4 includes a lag screw 4a and a barrel 4b. The implant assembly 2 is described in detail in U.S. Pat. No. 4,438,762, the disclosure of which is incorporated herein by reference in its entirety.

Figure 3:
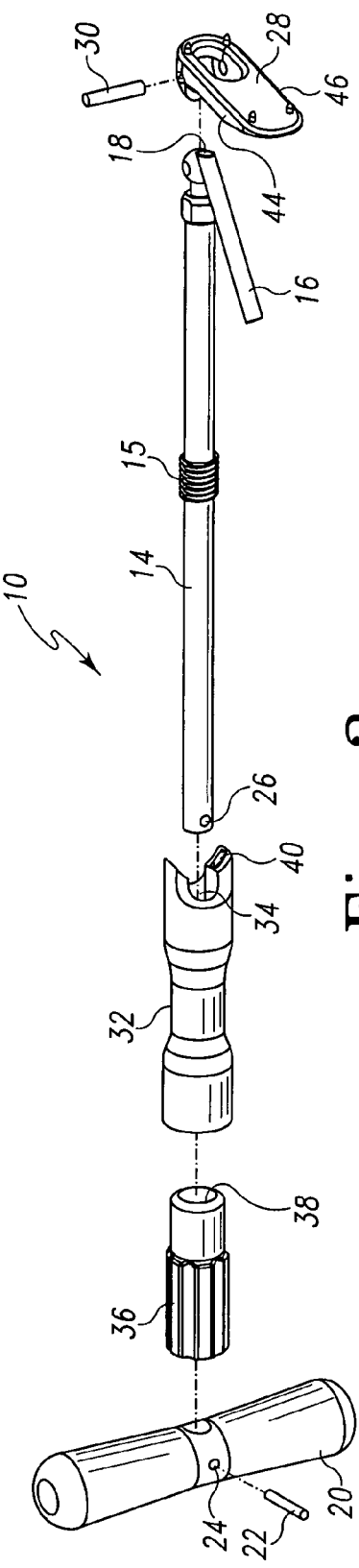
FIG. 3 is an exploded view of the guide assembly of FIG. 2.
Figure 4:
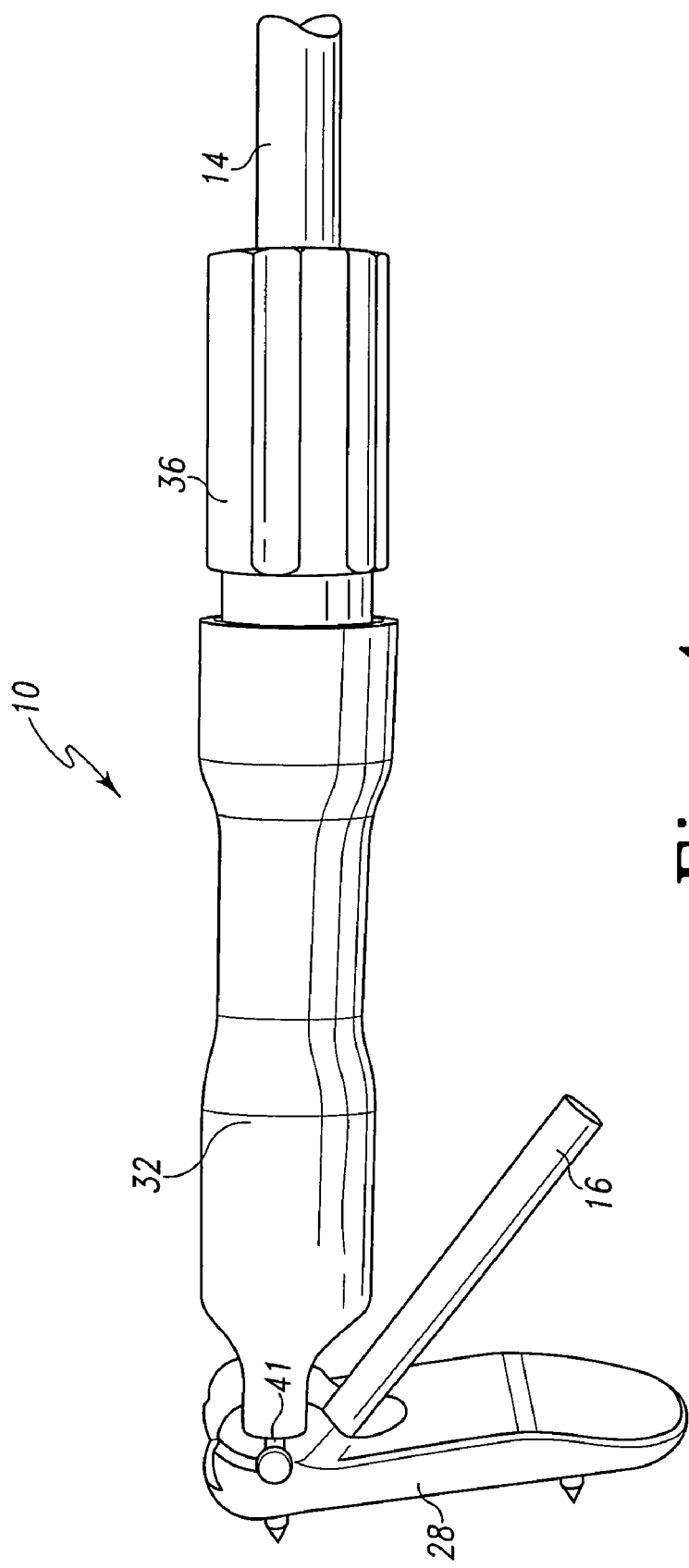
FIG. 4 is an enlarged, fragmentary elevational view of the guide assembly of FIG. 2, with the foot and the locking sleeve of the guide assembly possessing a first relative position.
Figure 5:
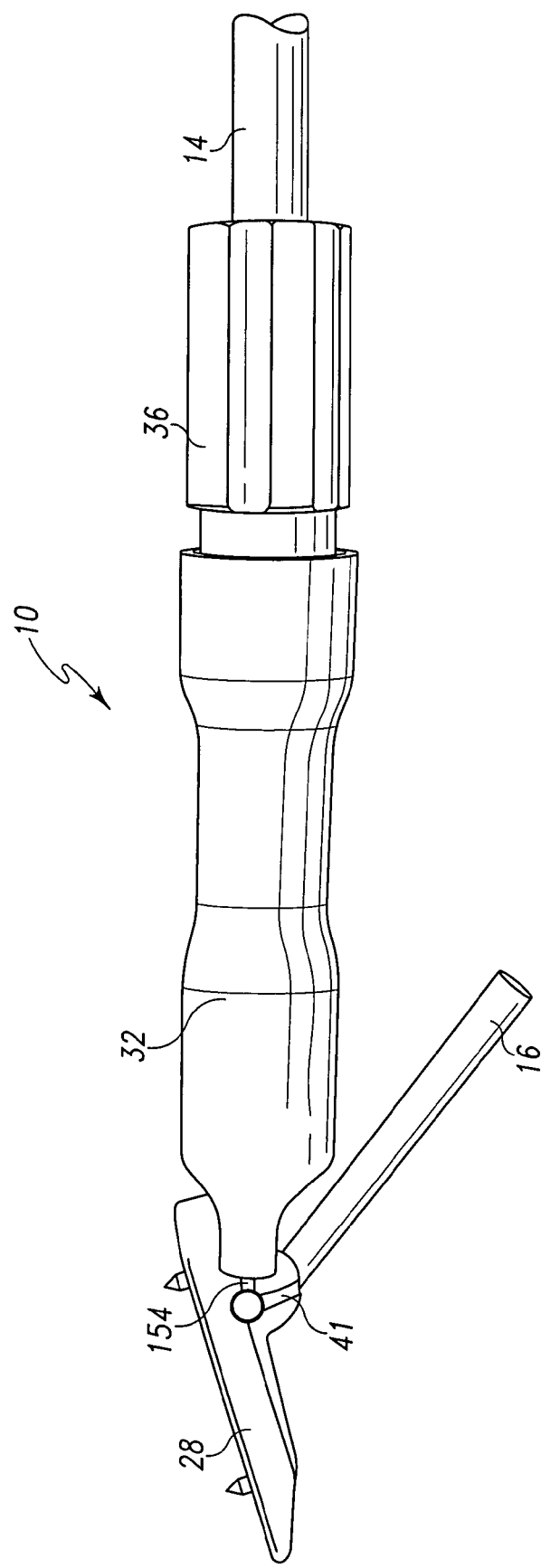
FIG. 5 is an enlarged, fragmentary elevational view of the guide assembly of FIG. 4, with the foot and the locking sleeve of the guide assembly possessing a second relative position.
Figure 6:
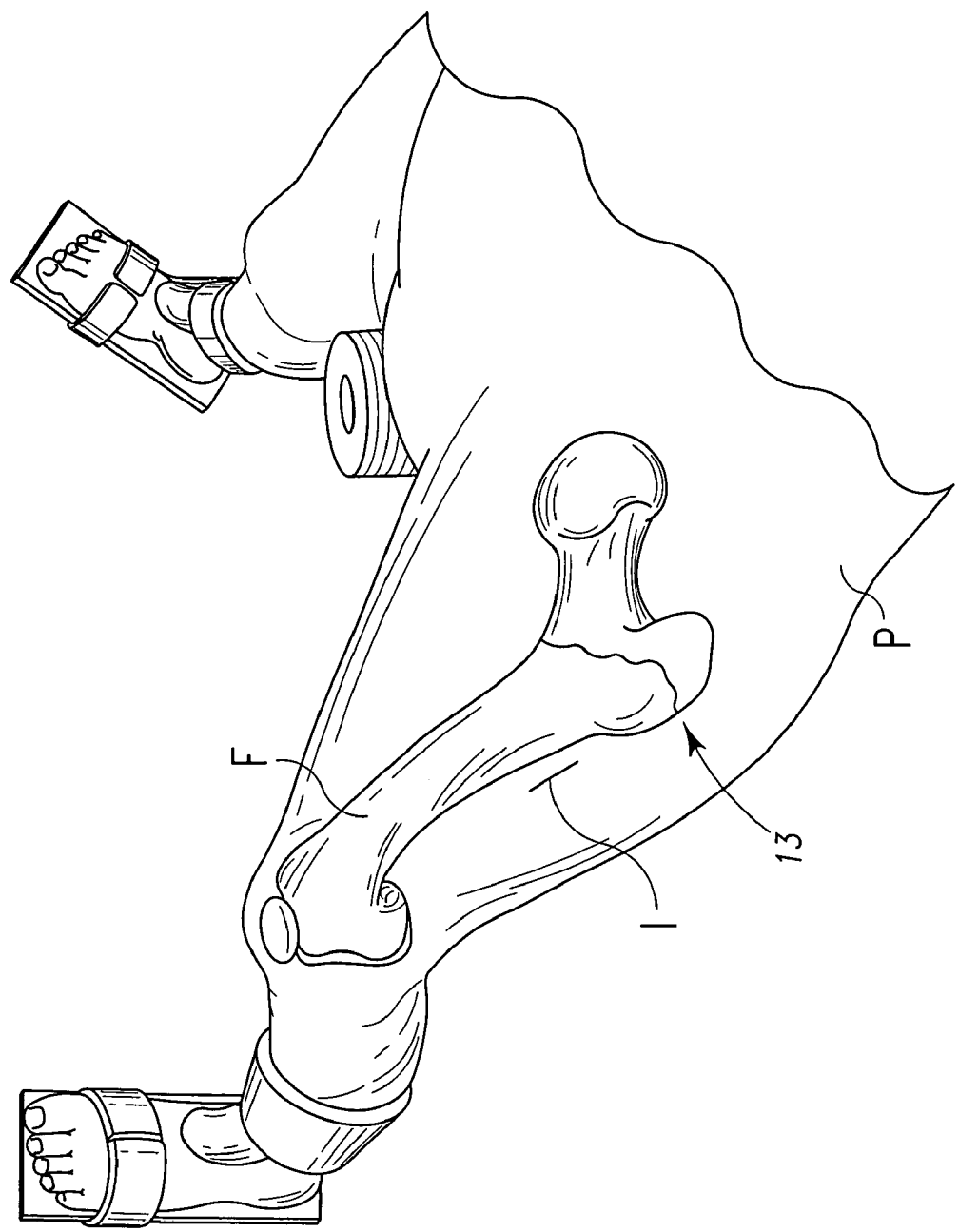
FIG. 6 is a fragmentary, perspective view of a patient with a fractured femur.
Figure 7:
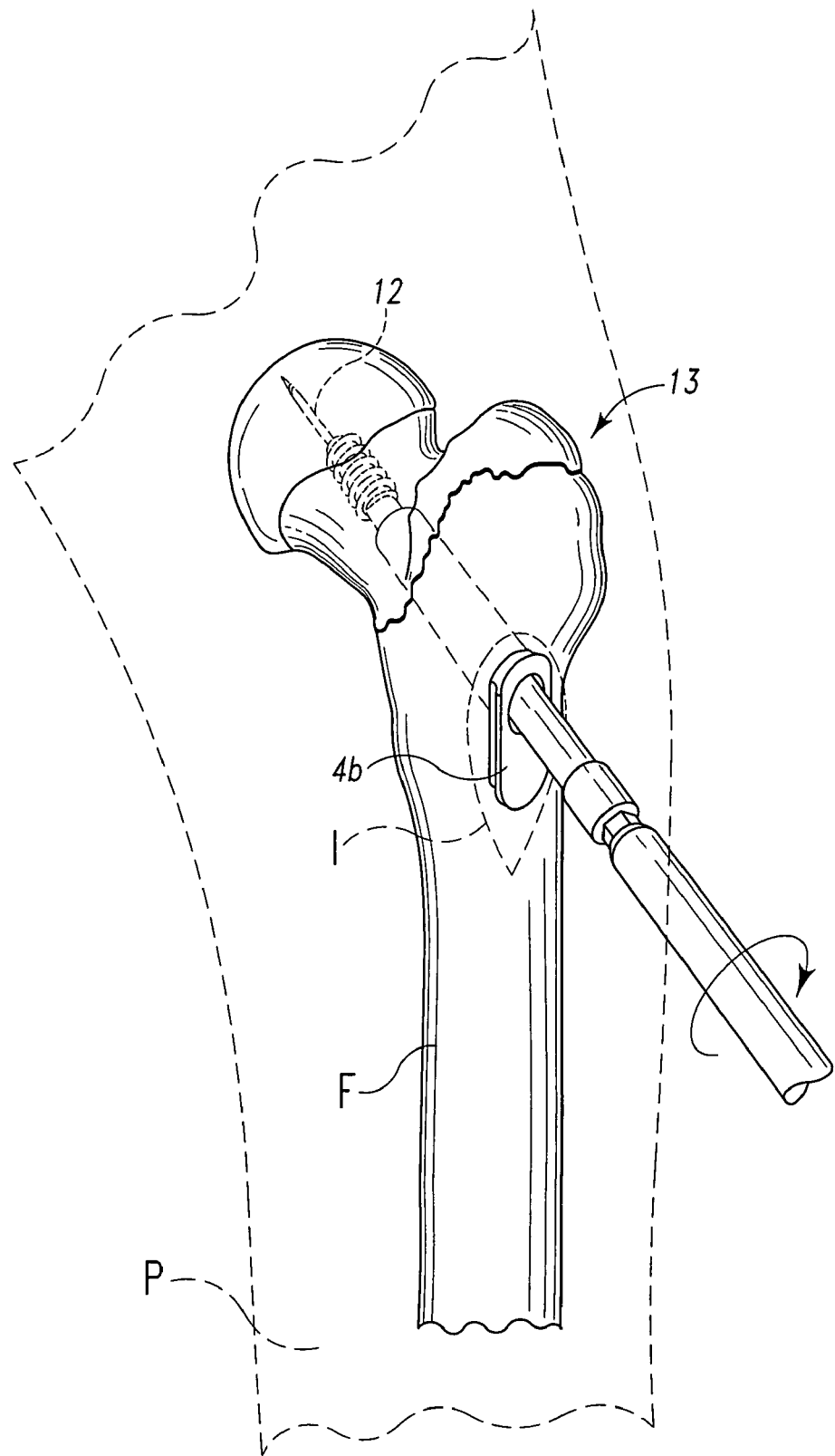
FIG. 7 is an enlarged, fragmentary view of the fractured femur of FIG. 6 undergoing a step of a medical procedure in accordance with the present disclosure.

An instrument that facilitates implantation of the captured screw assembly 4 is a guide assembly 10 shown in FIGS. 2-5. The guide assembly 10 is used to direct a guide pin 12 into a shaft, neck, and head of a femur such femur F shown in FIGS. 6 and 7 through an incision I in a patient P. Note that FIGS. 6 and 7 show a fracture 13 in the femur F. The guide assembly 10 includes a shaft 14 and a guide tube 16. The shaft 14 includes a set of external threads 15 as shown in FIG. 3. The guide tube 16 defines a lumen 18 through which the guide pin 12 may be advanced. The guide tube 16 is fixedly attached to the shaft 14 so that the guide tube 16 cannot move in relation to the shaft 14. The guide assembly 10 further includes a handle 20 that is attached to the shaft 14. A pin 22 is positioned within a bore 24 defined in the handle 20, as well as another bore 26 defined in the shaft 14. The guide assembly 10 further includes a foot 28 that is pivotably connected to the shaft 14. In particular, the foot 28 is configured to pivot in relation to the shaft 14 about a pin 30 from its position shown in FIG. 4 to its position shown in FIG. 5. The guide assembly 10 further includes a locking sleeve 32 that defines a passageway 34 through which the shaft 14 extends. The guide assembly 10 further includes a locking nut 36 that includes a passageway 38. The locking nut 36 includes a set of internal threads (not shown) located within the passageway 38 that meshingly engage with the set of external threads 15 of the shaft 14.

The locking sleeve 32 includes a tang 40 that may be urged into any of two grooves defined on the foot 28 so as to lock the foot 28 in relation to the shaft 14 in any of two fixed positions. Note that a third groove may be provided on the foot 28 to allow the foot 28 to be locked in a third position, namely, the position shown in FIG. 5 as will be discussed below.

The foot 28 has a first groove 41 defined therein. When the locking nut 36 is rotated in relation the shaft 14 in a first direction, the locking nut 36 urges the locking sleeve 32 toward the foot 28 until the tang 40 is advanced into the groove 41 thereby locking the foot 28 in fixed relation to the shaft 14 at the angle shown in FIG. 4. As will be discussed below, the foot 28 is locked at this position in relation to the shaft 14 during insertion of the guide pin 12 through the guide tube 16 and into the shaft, neck, and head of the femur F during a hip fracture reduction procedure. The position of the foot 28 relative to the shaft 14 may be adjusted by rotating the locking nut 36 in a direction opposite to the first direction discussed above thereby allowing the locking sleeve 32 to be advanced away from the foot 28. Once the tang 40 is advanced out of the groove 41, the foot 28 may be moved to its position shown in FIG. 5. As will be discussed below, the foot 28 assumes this position in relation to the shaft 14 during insertion (and removal) of the guide assembly 10 through the incision I of the patient P during the hip fracture reduction procedure.

As shown in FIGS. 2-5, the groove 41 is located on a first side 44 of the foot 28. The foot 28 includes another groove (not shown) on a second side 46 of the foot 28 at a location slightly offset from the location of the groove 41 on the first side 44. It should be appreciated that use of the groove 41 allows the foot 28 to be locked in fixed relation to the shaft 14 at the position shown in FIG. 4, while the use of the groove (not shown) defined on the second side 46 of the foot 28 allows the foot 28 to be locked in fixed relation to the shaft 14 at a position that is slightly different from the position shown in FIG. 4. For example, use of the groove (not shown) defined on the second side 46 of the foot 28 allows the foot 28 to be locked in fixed relation to the shaft 14 at an angle that is different by about 10 degrees in relation to the angle shown in FIG. 4. For example, the groove 41 is located on the foot 28 to cause the foot to be locked in fixed relation to the shaft so that an angle of 135.degree. is defined by the axis of the guide tube 16 and the axis of the foot 28, while the groove (not shown) on the second side 46 of the foot 28 is located on the foot to cause the foot to be locked in fixed relation to the shaft so that an angle of 145.degree is defined by the axis of the guide tube 16 and the axis of the foot 28.

Turning now to FIGS. 8-11, there is shown a plate holder assembly 50 that is used to facilitate implantation of the side plate 6 and the bone screws 8 of the implant assembly 2 into the patient P. The plate holder assembly 50 is used to retain the side plate 6 during insertion of the side plate 6 through the incision I in the patient P. The plate holder assembly 50 includes a shaft 52, a handle assembly 54, a holder (or inner collet) 56, an actuator (or outer collet) 58, a foot 60, a driver (or locking nut) 62, and a locking ring 64.

Figure 12:
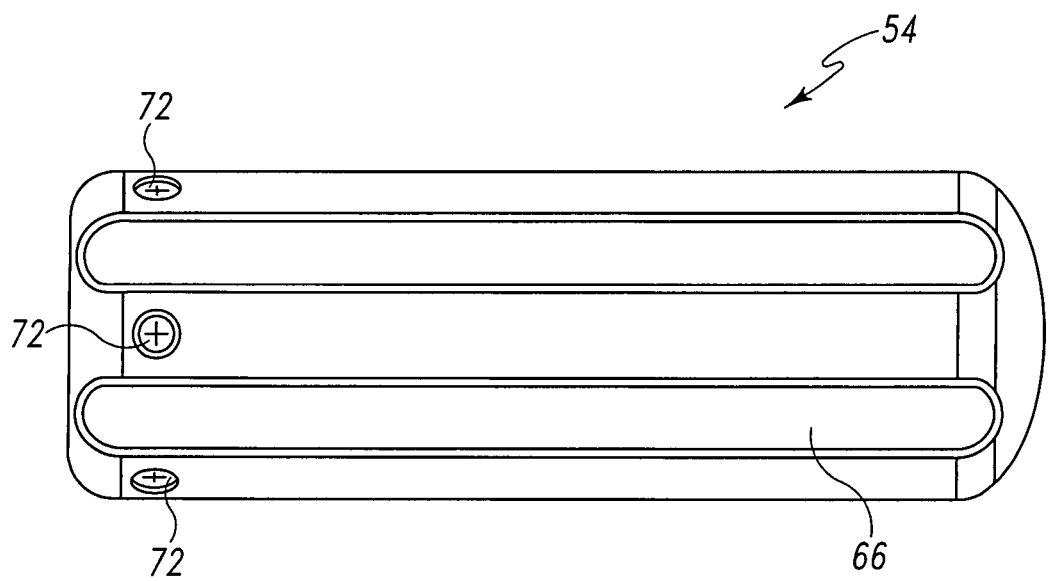
FIG. 12 is a side elevational view of the handle assembly of the plate holder assembly of FIG. 9.
Figure 13:
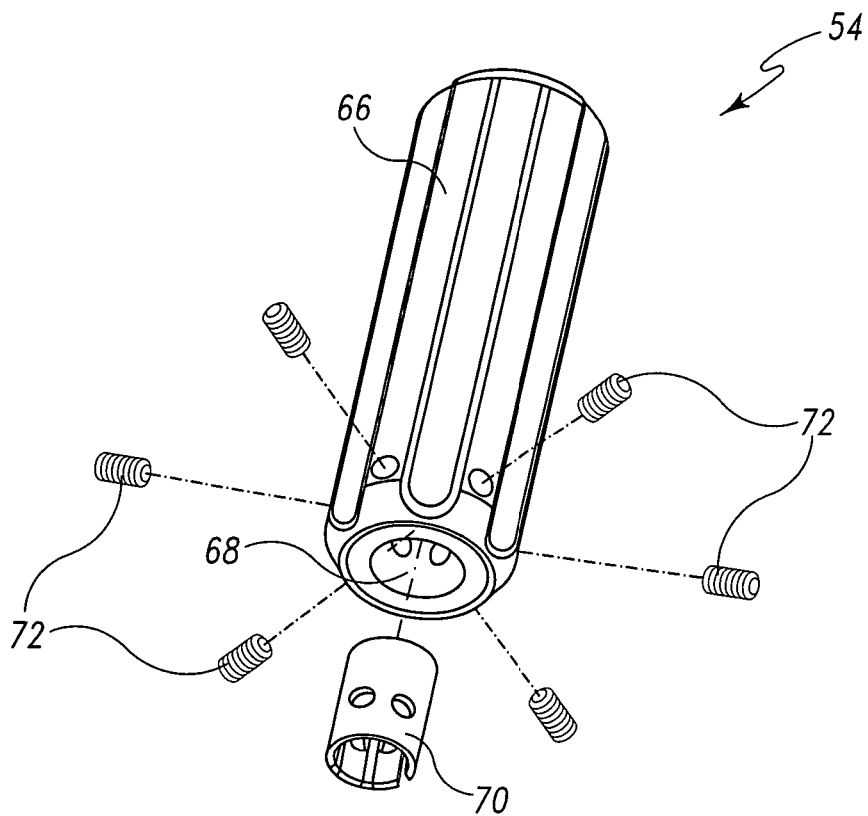
FIG. 13 is an exploded view of the handle assembly of the plate holder assembly of FIG. 9.

As shown in FIGS. 12-13, the handle assembly 54 includes a handle member 66 defining a recess 68, and an insert 70 located within the recess 68. Also located within the recess 68 is a plurality of ball plungers 72 that cooperate with the insert 70 to releasably secure the handle member 66 to the shaft 52.

Figure 14:
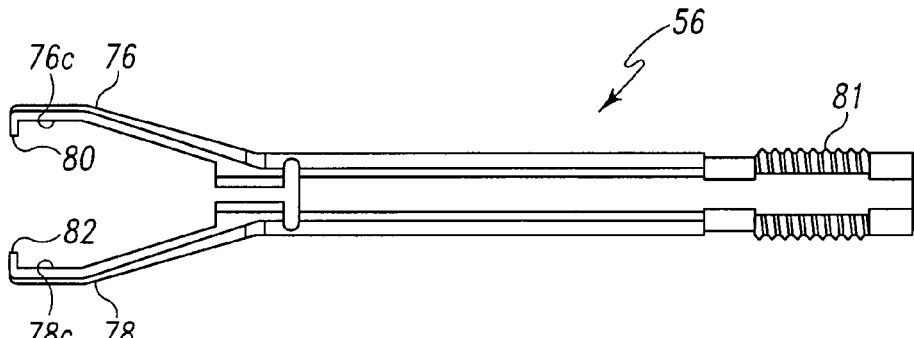
FIG. 14 is a top elevational view of the holder of the plate holder assembly of FIG. 9.
Figure 15:
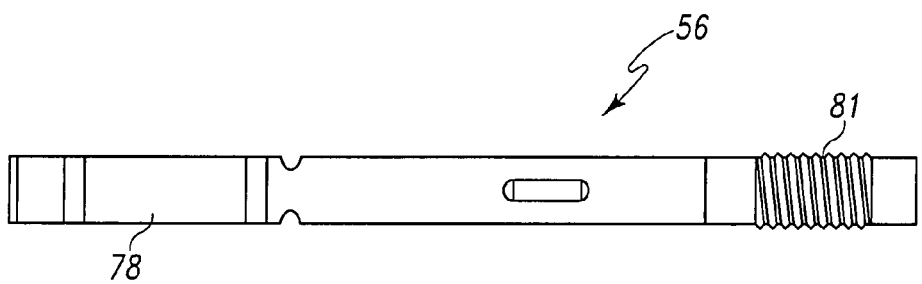
FIG. 15 is a side elevational view of the holder of the plate holder assembly of FIG. 9.
Figure 16:
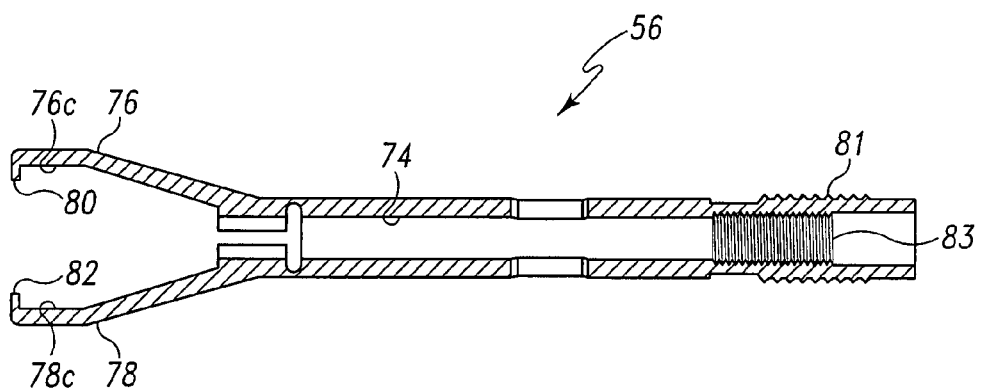
FIG. 16 is a cross sectional view of the holder of the plate holder assembly of FIG. 9.
Figure 17:
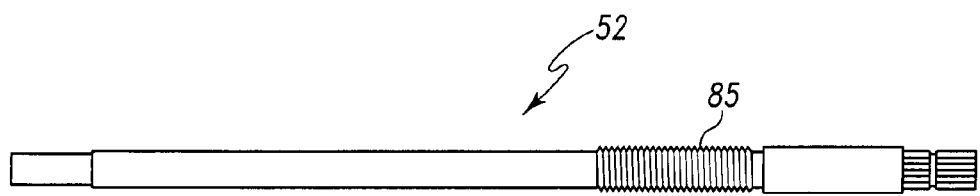
FIG. 17 is a side elevational view of the shaft of the plate holder assembly of FIG. 9.
Figure 18:
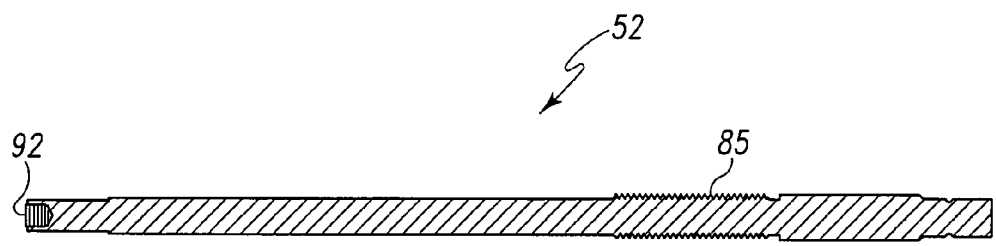
FIG. 18 is a cross sectional view of the shaft of the plate holder assembly of FIG. 9.

FIGS. 14-16 show the holder 56 in more detail. In particular, the holder 56 defines a central passageway 74 which is configured to receive the shaft 52. The holder 56 includes an arm 76 and an arm 78 that are spaced apart from each other. The arm 76 includes an inwardly extending projection 80, while the arm 78 includes an inwardly extending projection 82. The holder 56 has a set of external threads 81 as shown in FIGS. 14-16. The holder 56 further has a set of internal threads 83 located within the central passageway 74. The set of internal threads 83 is configured to meshingly engage a set of external threads 85 of the shaft 52. The set of external threads of shaft 52 are shown in FIGS. 17-18.

Figure 19:
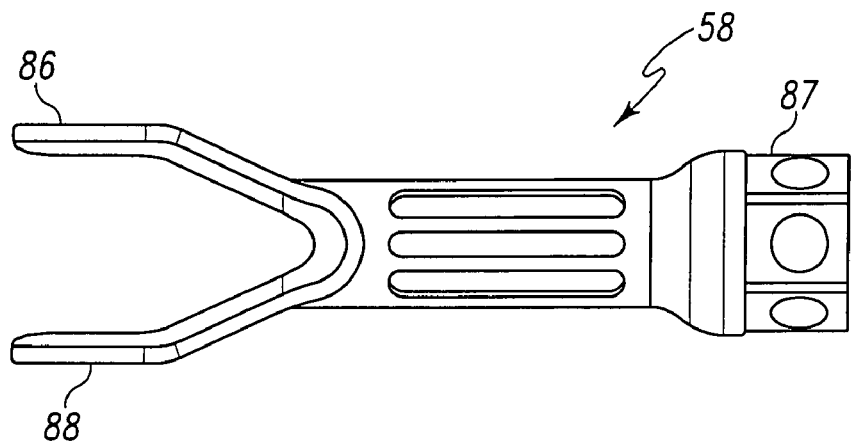
FIG. 19 is a top elevational view of the actuator of the plate holder assembly of FIG. 9.
Figure 20:
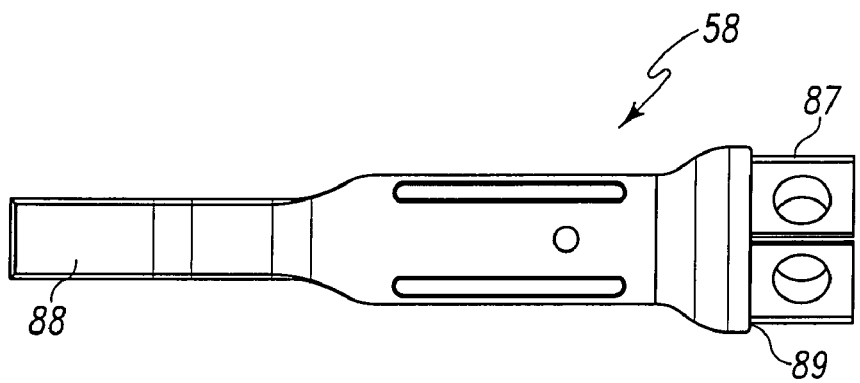
FIG. 20 is a side elevational view of the actuator of the plate holder assembly of FIG. 9.
Figure 21:
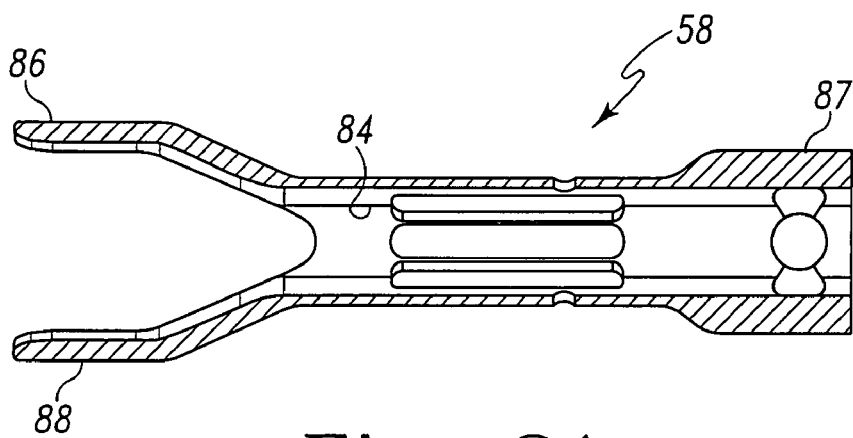
FIG. 21 is a cross sectional view of the actuator of the plate holder assembly of FIG. 9.
Figure 22:
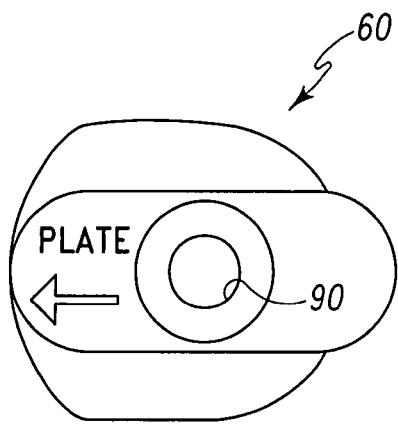
FIG. 22 is a bottom elevational view of the foot of the plate holder assembly of FIG. 9.
Figure 23:
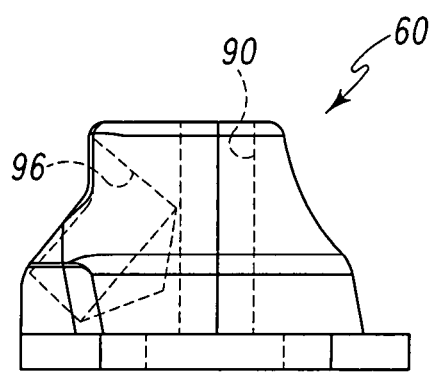
FIG. 23 is a side elevational view of the foot of the plate holder assembly of FIG. 9.
Figure 24:
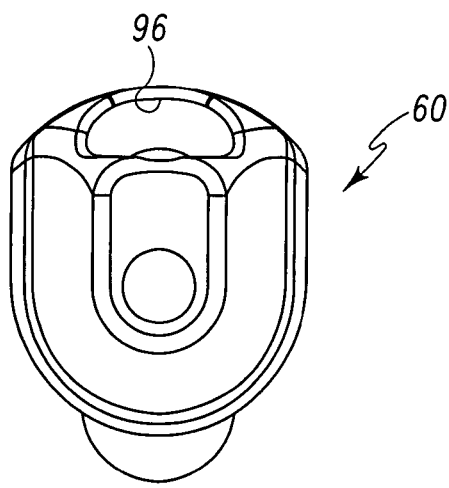
FIG. 24 is a top elevational view of the foot of the plate holder assembly of FIG. 9.
Figure 25:
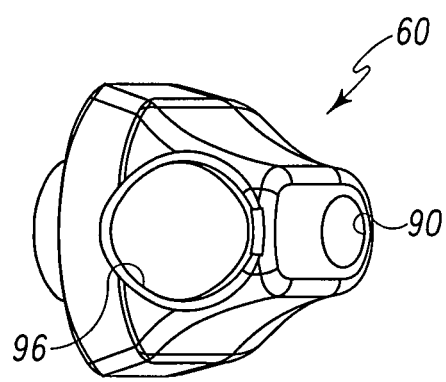
FIG. 25 is a perspective view of the foot of the plate holder assembly of FIG. 9.

FIGS. 19-21 show the actuator 58 in more detail. In particular, the actuator 58 defines a central passageway 84 which is configured to receive the holder 56. The actuator 58 includes an arm 86 and an arm 88 that are spaced apart from each other. At a proximal end portion of the actuator 58, there is defined a polygonal-shaped exterior surface 87. Preferably, the polygonal-shaped surface 87 is hexagonal-shaped. Alternatively, the surface 87 may possess other polygonal shapes such as rectangular and octagonal. The actuator 58 further includes a ledge that defines a clamping surface 89.

Figure 11:
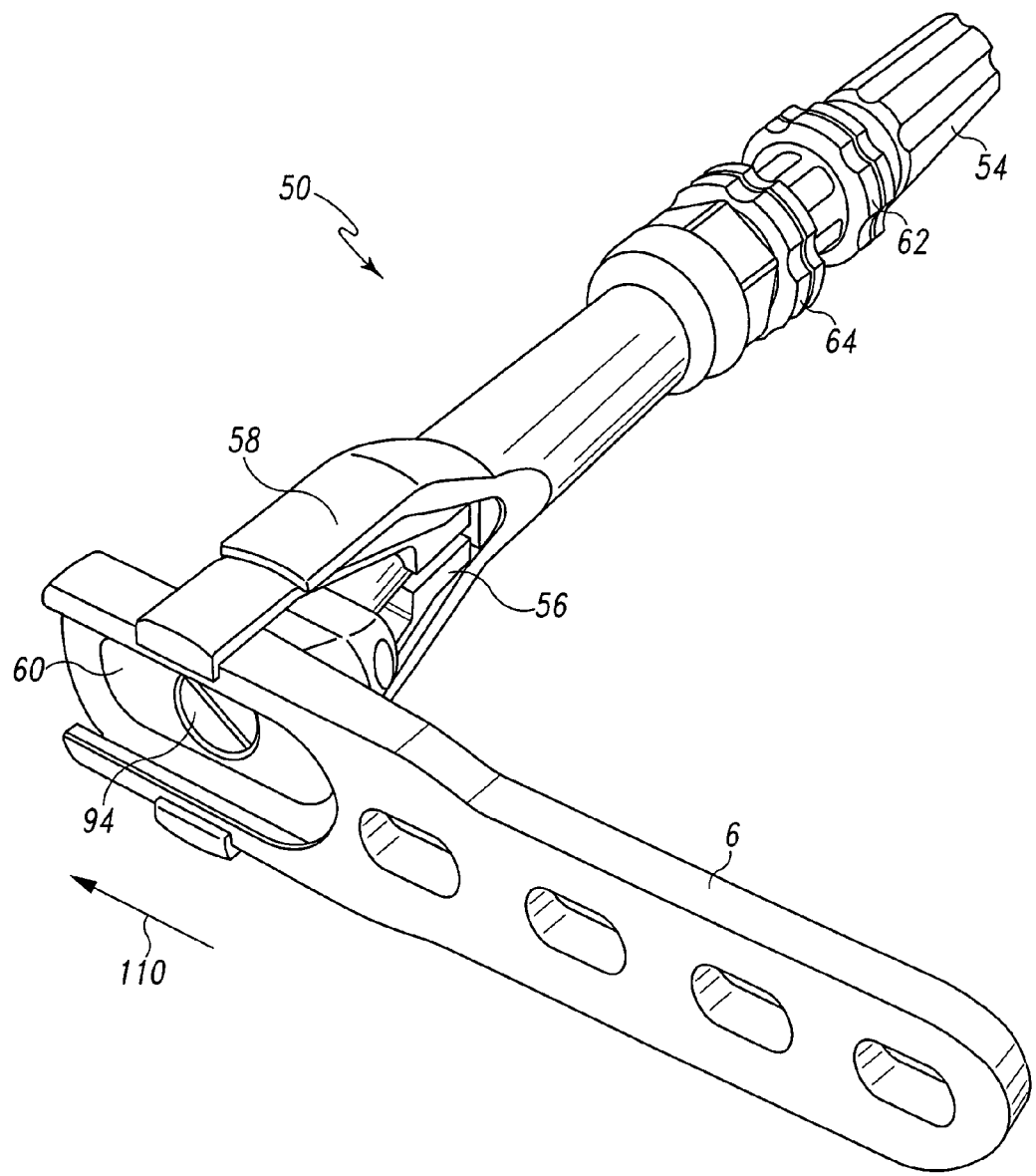
FIG. 11 is another perspective view of the plate holder assembly of FIG. 8 with the side plate being retained between its arms.
Figure 26:
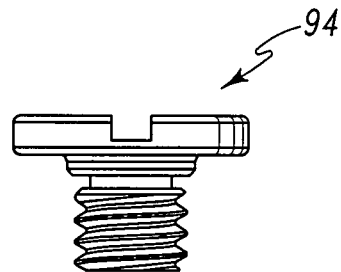
FIG. 26 is a side elevational view of the fastener of the plate holder assembly of FIG. 9.

Turning now to FIGS. 22-25, the foot 60 is shown in more detail. The foot 60 includes a passageway 90 that is configured to receive a distal end of the shaft 52. Note that the distal end portion of the shaft 52 has defined therein a fastener bore 92 as shown in FIG. 18. When the distal end of the shaft 52 is located within the passageway 90, a fastener 94 (shown in FIG. 26) is threadingly engaged to within the fastener bore 92 to secure the foot 60 to the shaft 52. FIG. 11 shows the fastener 94 securing the foot 60 to the shaft 52. It should be appreciated that the shaft 52, the foot 60, and the fastener 94 are configured such that when the foot 60 is secured to the shaft 52 by the fastener 94, the shaft 52 is free to rotate 360 degrees in relation to the foot 60. The foot 60 further includes an impactor recess 96 configured to receive the distal end of an impactor 112 (see FIG. 30). It should be appreciated that the foot 60 and shaft 52 of the plate holder assembly collectively operate as a press to urge the side plate 6 into contact with the projections 80, 82 of the holder arms 76, 78.

Figure 27A:
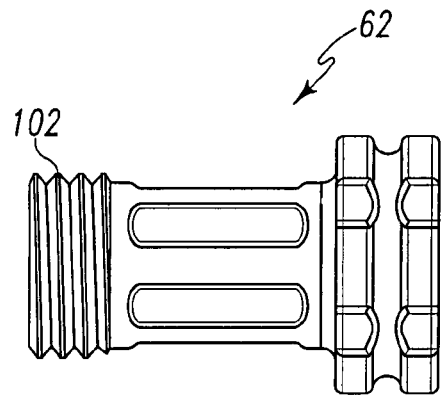
FIG. 27A is a side elevational view of the driver of the plate holder assembly of FIG. 9.
Figure 27B:
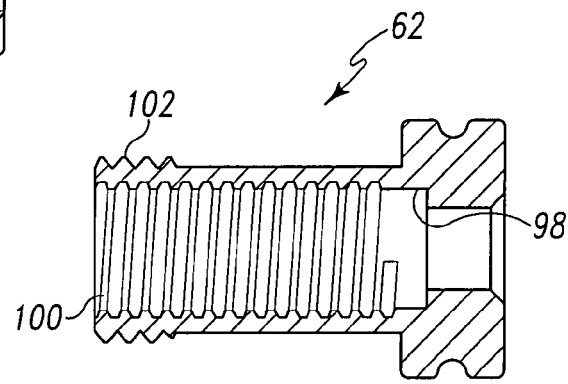
FIG. 27B is a cross sectional view of the driver of the plate holder assembly of FIG. 9.

FIGS. 27A and 27B show the driver 62 in more detail. The driver 62 includes a central passageway 98. A set of internal threads 100 are located within the central passageway 98. The driver 62 also includes a set of external threads 102 as shown in FIGS. 27A and 27B. The set of internal threads 100 is configured to meshingly engage the set of external threads 81 of the holder 56.

Figure 28:
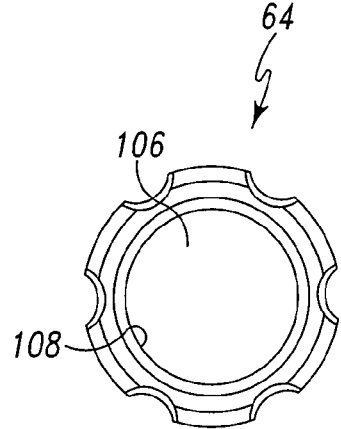
FIG. 28 is an end elevational view of the locking ring of the plate holder assembly of FIG. 9.
Figure 29:
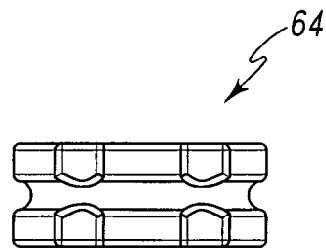
FIG. 29 is a side elevational view of the locking ring the plate holder assembly of FIG. 9.

FIGS. 28-29 show the show the locking ring 64 in more detail. The locking ring 64 includes a central passageway 106. A set of internal threads 108 are located within the central passageway 106. The set of internal threads 108 is configured to meshingly engage the set of external threads 102 of the driver 62.

Figure 10:
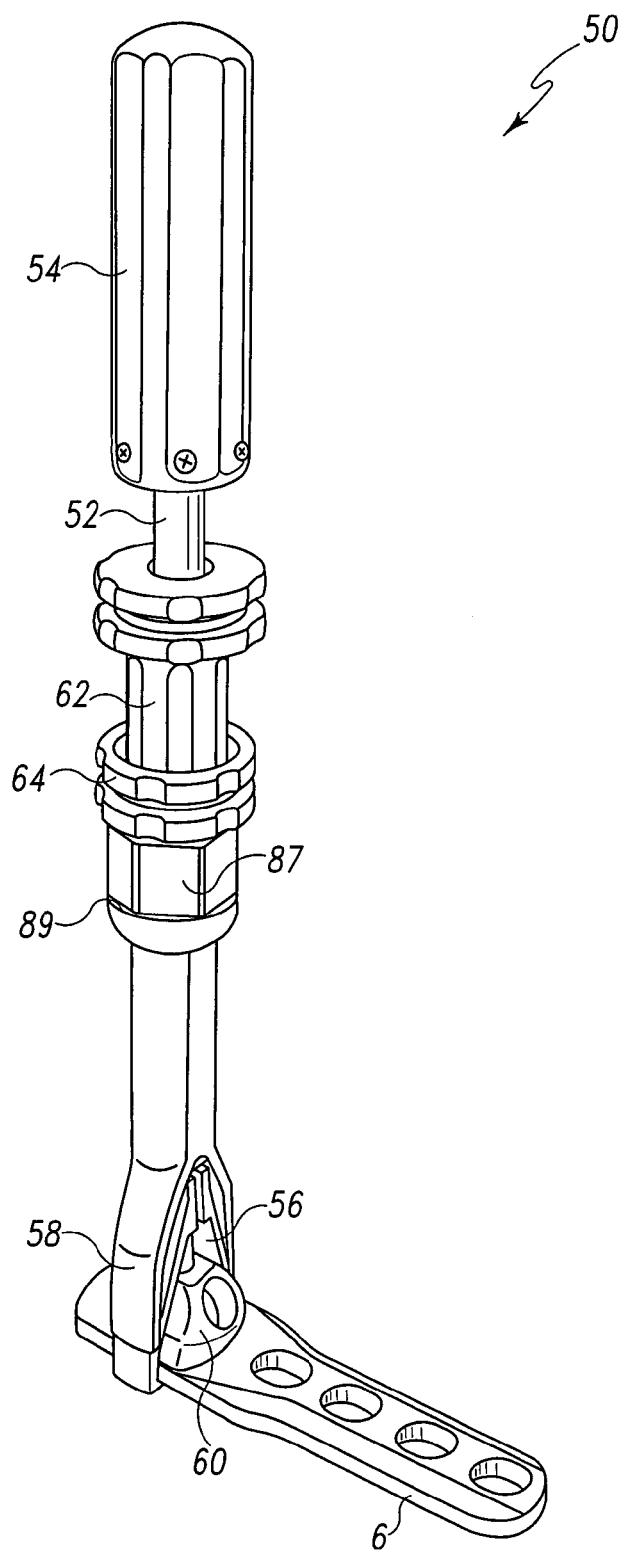
FIG. 10 is a perspective view of the plate holder assembly of FIG. 8 with a side plate being retained between its arms.

When assembled, the plate holder assembly 50 is configured to releasably retain the side plate 6 as shown in FIGS. 10 and 11. Thus, in order to manipulate the plate holder assembly from its position in FIG. 8 to a position in which a side plate may be inserted between the foot 60 and the projections 80, 82 of the holder arms 76, 78, the following manipulations must occur. The foot 60 must be move moved away from the projections 80, 82, and the holder arms 76, 78 must be moved outwardly relative to each other.

In order to move the foot 60 away from the projections 80, 82, the handle assembly 54 and thus the shaft 52 are rotated in a first direction in relation to the holder 56. This rotation causes axial displacement of the shaft 52 in relation to the holder 56 thereby moving the foot 60 axially away from the projections 80, 82.

Figure 8:
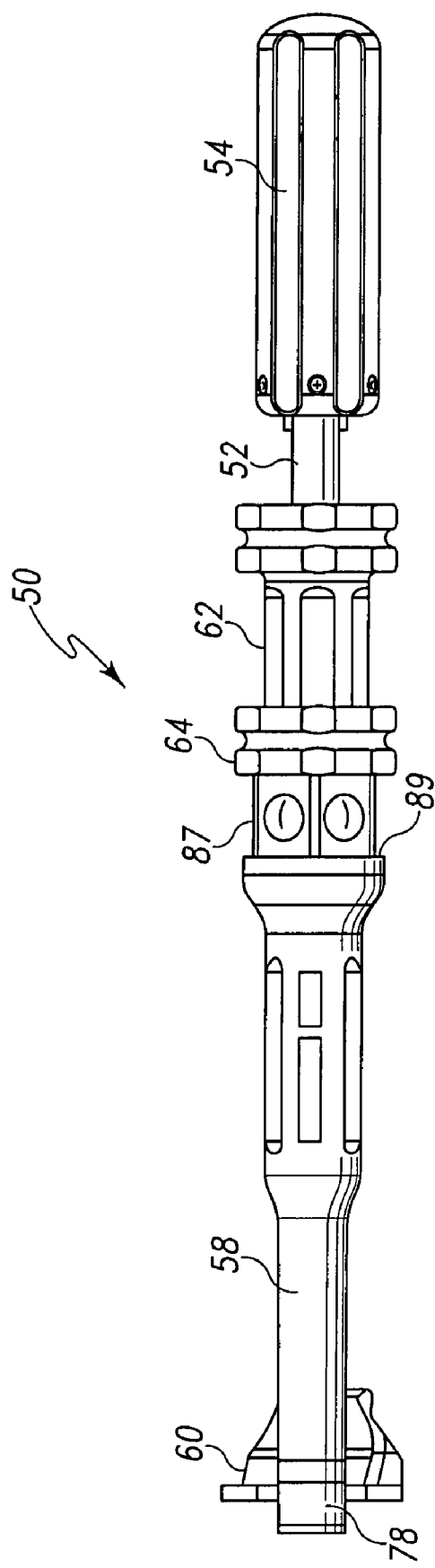
FIG. 8 is a side elevational view of the plate holder assembly that is used in the implantation of the implant assembly of FIG. 1 according to the present disclosure.
Figure 9:
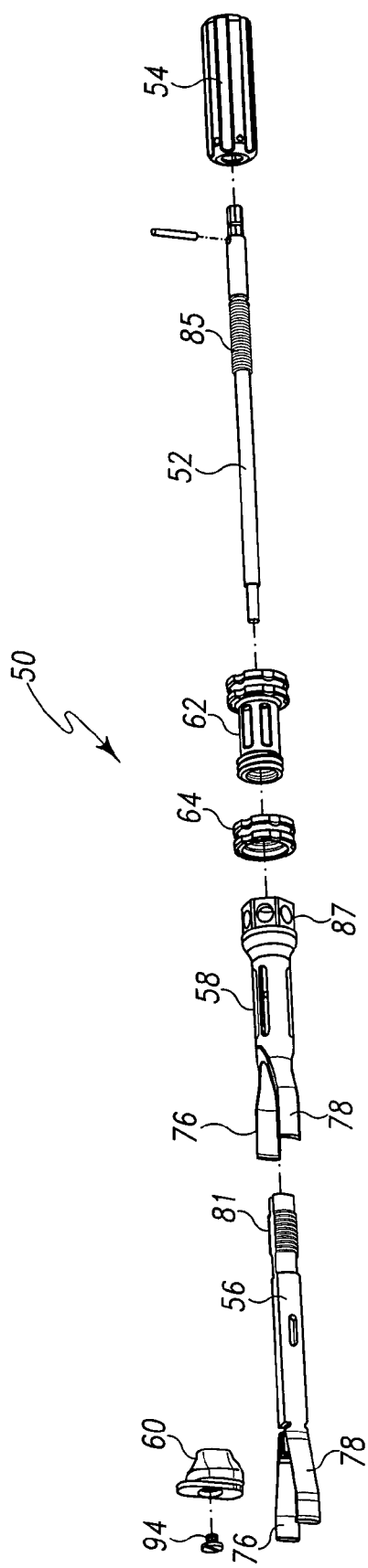
FIG. 9 is an exploded view of the plate holder assembly of FIG. 8.

In order to move the holder arms 76, 78 outwardly, the driver 62 is rotated in a first direction thereby causing the driver to be advanced toward the handle assembly 54 and away from the actuator 58. A space is thereby created which allows the actuator 58 to be advanced toward the handle assembly 54 and away from the foot 60. Note that prior to advancement of the actuator 58 (at the relative positioning of the actuator 58 and holder 56 shown in FIG. 8), the arms 86, 88 of the actuator are respectively urged into contact with the arms 76, 78 of the holder 56 thereby biasing the holder arms 76, 78 a distance inwardly. As the actuator 58 is advanced toward the handle assembly 54 as set forth above, the actuator arms 86, 88 are advanced axially and out of contact with the holder arms 76, 78 thereby allowing the holder arms 76, 78 to spring outwardly. The arm 76 defines a bone plate contact portion 76C on a surface thereof, while the arm 78 defines a bone plate contact portion 78C as shown in FIGS. 14 and 16. When the actuator 58 and holder 56 are positioned as shown in FIG. 8, the bone plate contact portion 76C and the bone plate contact portion 78C are separated by a first distance. However, after the actuator 58 is advanced toward the handle assembly 54 a distance as discussed above, the holder arms 76, 78 spring outwardly so that the bone plate contact portion 76C and the bone plate contact portion 78C are now separated by a second distance which is greater than the first distance. While the bone plate contact portions 76C, 78C are separated by the second distance, the side plate 6 may be inserted between the foot 60 and the projections 80, 82 of the holder arms 76, 78 in the direction shown by arrow 110 in FIG. 11.

In order to insert the side plate 6 between the foot 60 and the projections 80, 82, the side plate 6 is advanced in the direction indicated by arrow 110 in FIG. 11 until the foot 60 is aligned with the largest opening of the side plate 6. Thereafter, the handle assembly 54 and thus the shaft 52 is rotated in a second direction in relation to the holder 56, opposite to the first direction discussed above. This rotation causes the axial displacement of the shaft 52 in relation to the holder 56 thereby moving the foot 60 axially toward the projections 80, 82. This rotation is continued until the side plate 6 becomes clamped between the foot 60 and the projections 80 and 82. Then, the driver 62 is rotated in a second direction, opposite the first direction discussed above, so as to cause the driver to be advanced toward the foot 60. Advancement of the driver toward the foot 60 thereby causes the actuator arms 86, 88 to be advanced toward the holder arms 76, 78. Continued advancement of the actuator arms 86, 88 results in the actuator arms 86, 88 slidingly contacting the holder arms 76, 78 thereby urging them inwardly. Inward movement of the holder arms 76, 78 causes the bone plate contact portions 76C, 78C to clamp the side plate 6 therebetween as shown in FIG. 11.

With the side plate 6 securely retained between the bone plate contact portions 76C, 78C, as well as between the foot 60 and the projections 80, 82 of the holder arms 76, 78 as described above, the side plate 6 may be inserted through the incision I in the patient P with the assistance of the plate holder assembly 50.

Figure 30:
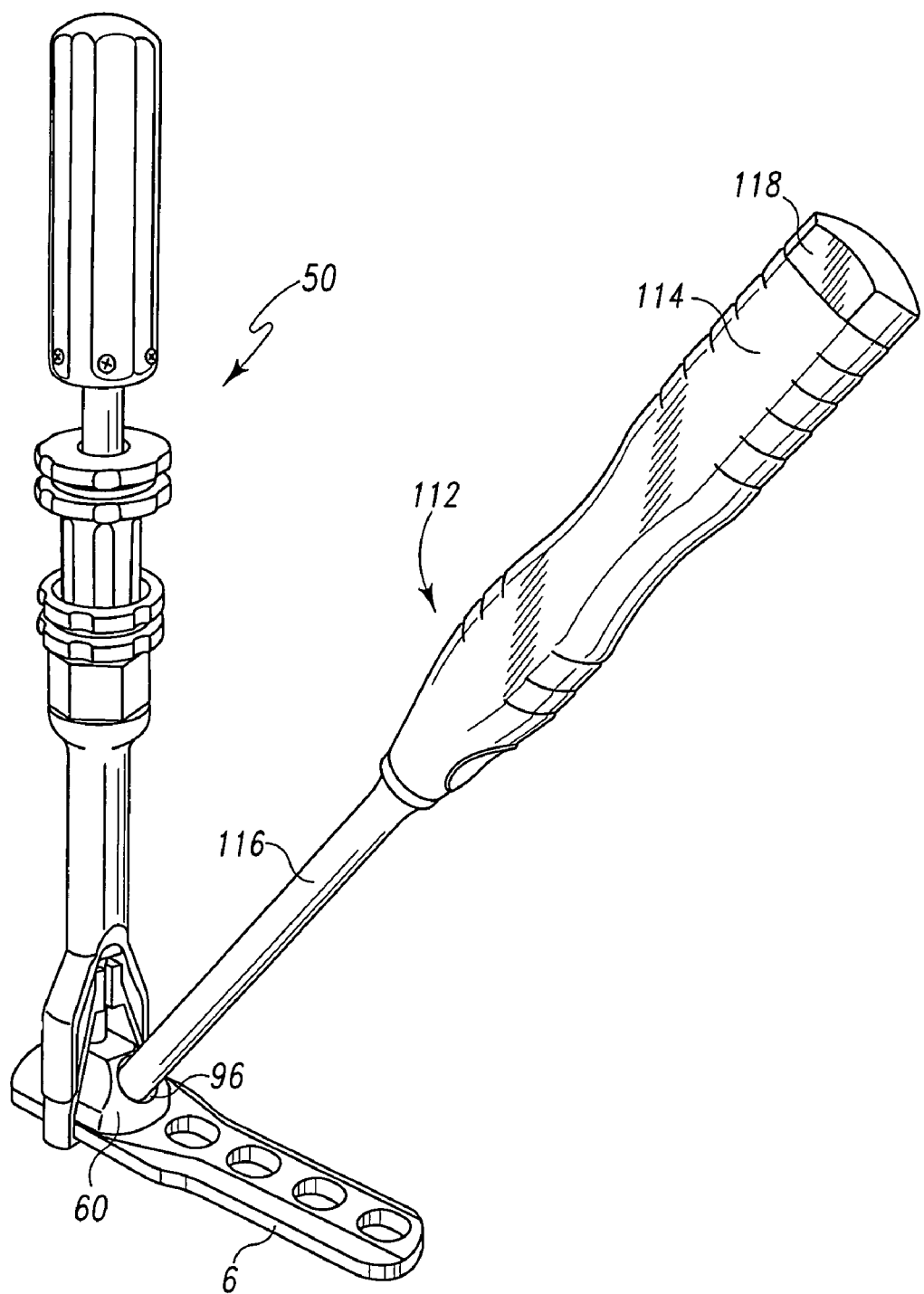
FIG. 30 is a perspective view of the plate holder assembly of FIG. 8 retaining a side plate between its arms and having an impactor retained within a foot of the plate holder assembly.
Figure 31:
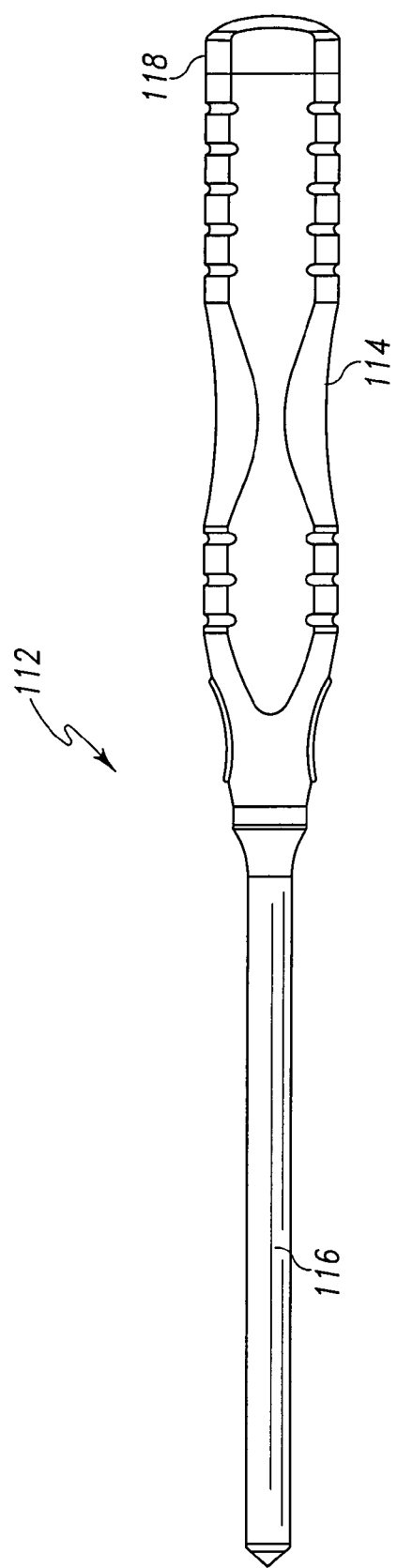
FIG. 31 is a side elevational view of the impactor shown in FIG. 30.

After the side plate 6 is inserted through the incision I, the side plate 6 is manipulated with the plate holder assembly 50 to mate the side plate 6 to the barrel 4b of the captured screw assembly 4 inside the wound. To ensure snug mating, the distal end of the impactor 112 is inserted into the impactor recess 96 of the foot 60 as shown in FIG. 30. Thereafter, the proximal end of the impactor is tapped three or four times with a mallet to transfer force to the side plate 6 to ensure that the side plate 6 and the barrel 4b are fully mated. The impactor 112 is shown in more detail in FIG. 30. In particular, the impactor 112 includes a handle 114, a shaft 116, and a strike cap 118. The shaft 116 is connected to a distal end of the handle 114, while the strike cap 118 is connected to a proximal end of the handle 114.

Figure 32:
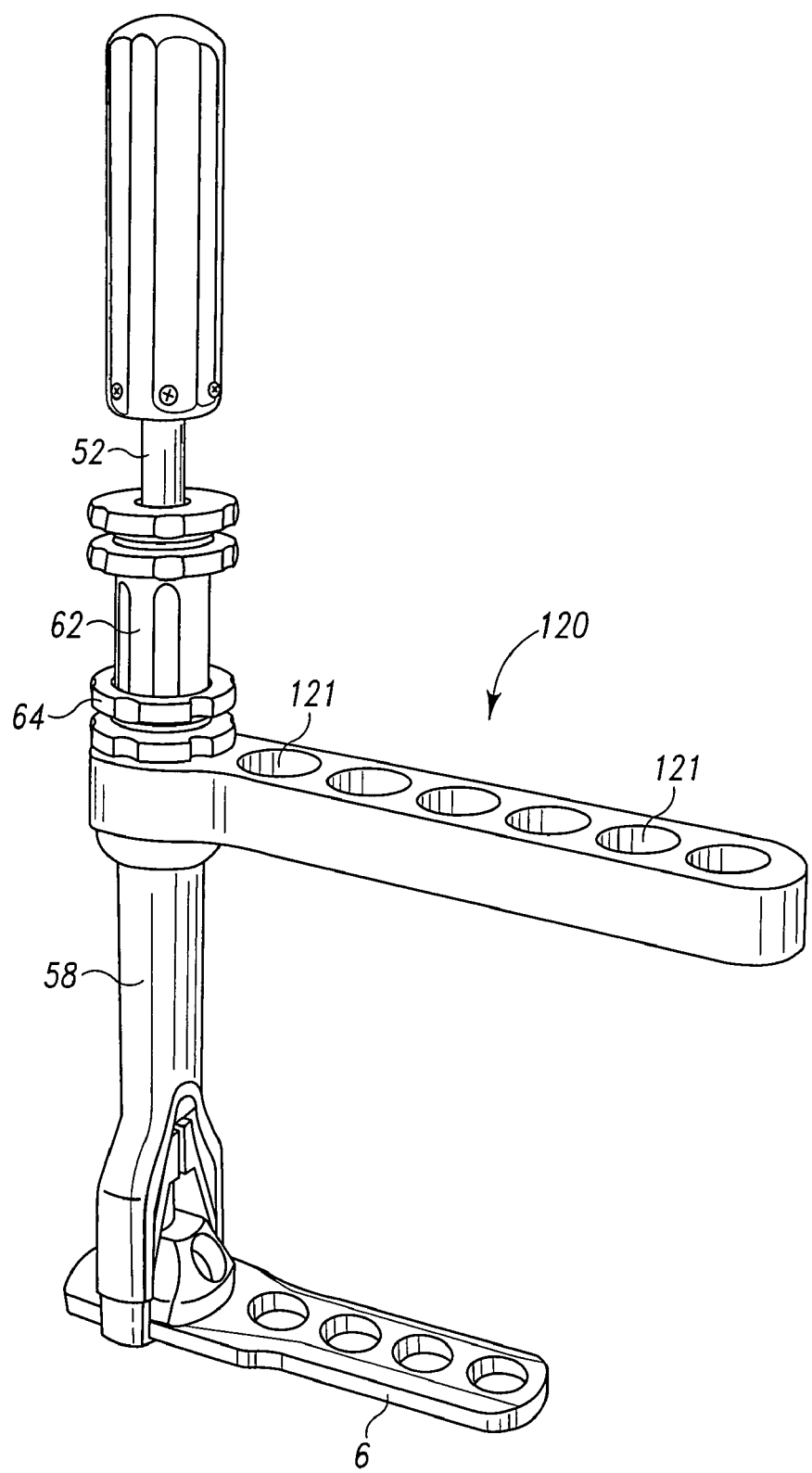
FIG. 32 is a perspective view of the plate holder assembly of FIG. 8 retaining a side plate between its arms and having a targeting component attached to the actuator of the plate holder assembly.
Figure 33:
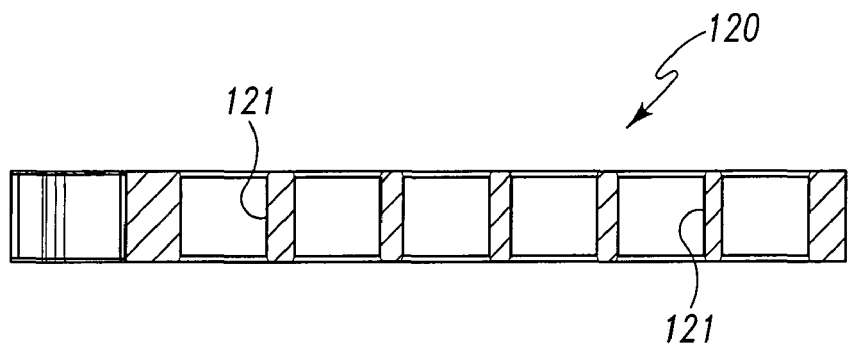
FIG. 33 is a cross sectional view of the targeting component shown in FIG. 32.
Figure 34:
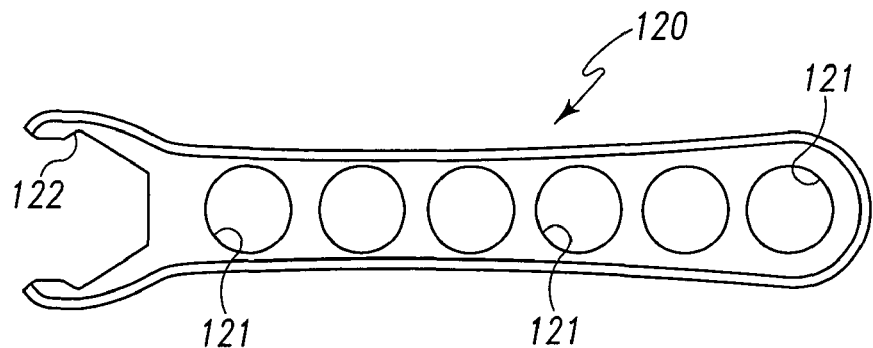
FIG. 34 is a top elevational view of the targeting component shown in FIG. 32.
Figure 35:
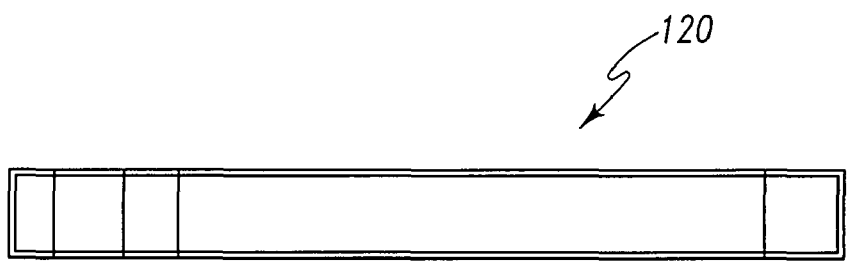
FIG. 35 is a side elevational view of the targeting component shown in FIG. 32.

Once the side plate 6 is fully mated with the barrel 4b of the captured screw assembly 4, the distal end of the impactor 112 is removed from the impactor recess 96 and a targeting component 120 is attached to the actuator 56 as shown in FIG. 32. The targeting component 120 component is shown in more detail in FIGS. 33-35. The targeting component 120 defines a plurality of holes 121. In addition, the targeting component 120 includes a mating surface 122 that is configured to be at least partially complementary to the polygonal-shaped surface 87 of the actuator 58. In order to attach the targeting component 120 to the actuator 56, the targeting component is advanced toward the actuator until the mating surface 122 mates with the polygonal-shaped surface 87. Thereafter, the locking ring 64 is rotated in relation to the driver 62 thereby advancing the locking ring 64 toward the targeting component 120. Further advancement of the locking ring 64 causes the locking ring to contact and clamp the targeting component 120 between the locking ring 64 and the clamping surface 89 of the actuator 58 as shown in FIG. 32.

Figure 36:
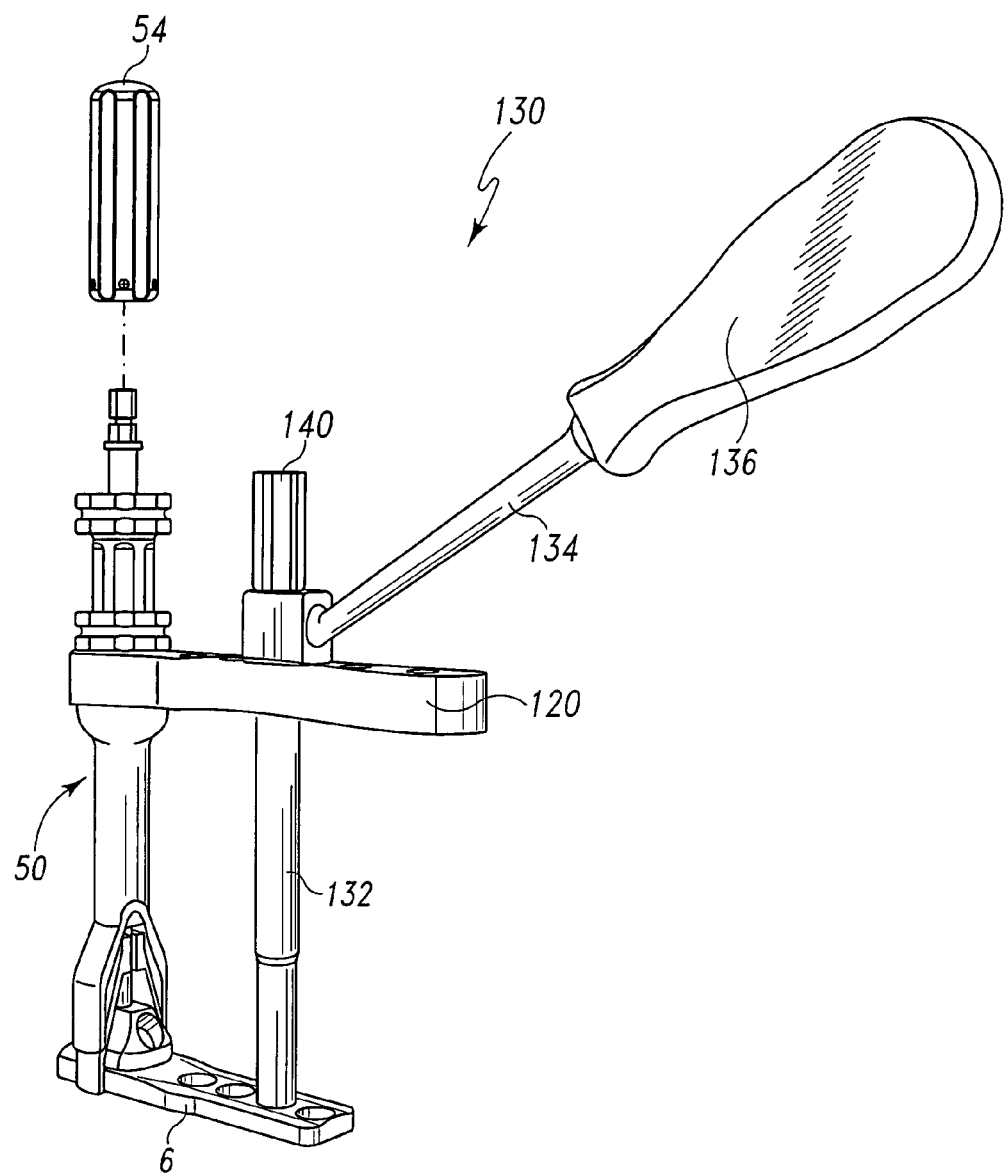
FIG. 36 is a perspective view of the plate holder assembly of FIG. 8 retaining a side plate between its arms and having a targeting component attached to the actuator of the plate holder assembly, and further having a subassembly of a drill guide assembly extending through one of the holes defined in the targeting component, and additionally showing the handle assembly separated from the shaft.
Figure 40:
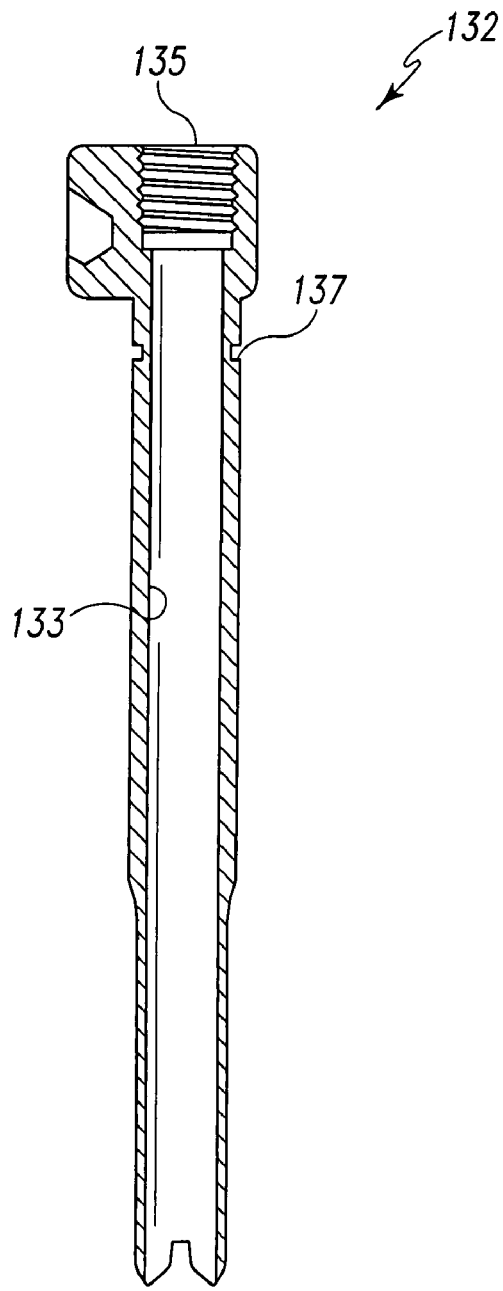
FIG. 40 is a cross sectional view of the outer sheath of the subassembly of the drill guide assembly shown in FIG. 37.
Figure 41:
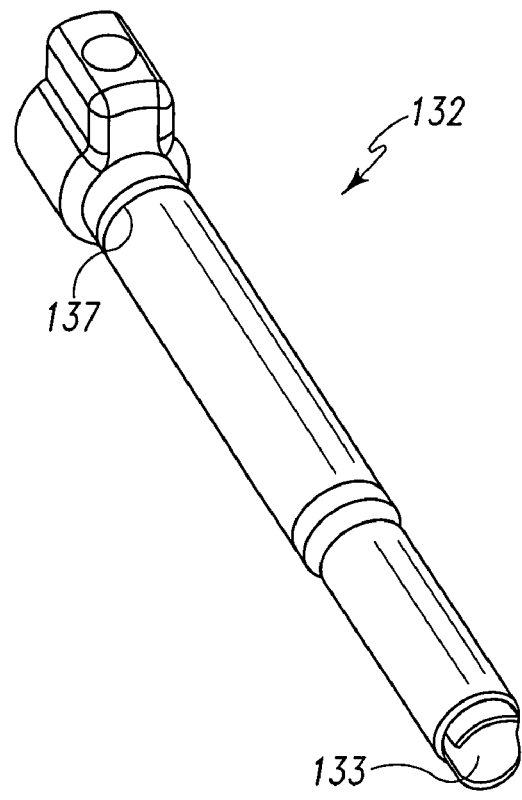
FIG. 41 is a side elevational view of the outer sheath of the subassembly of the drill guide assembly shown in FIG. 37.
Figure 42:
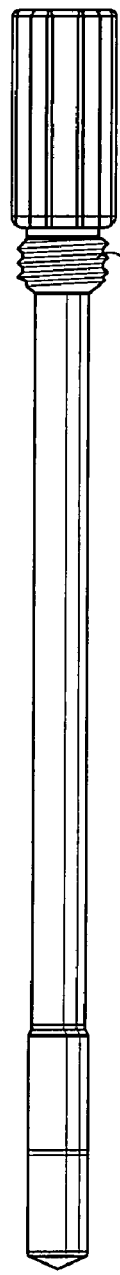
FIG. 42 is a side elevational view of the trocar of the subassembly of the drill guide assembly that is configured to extend through the central passageway of the outer sheath shown in FIG. 37.
Figure 43:
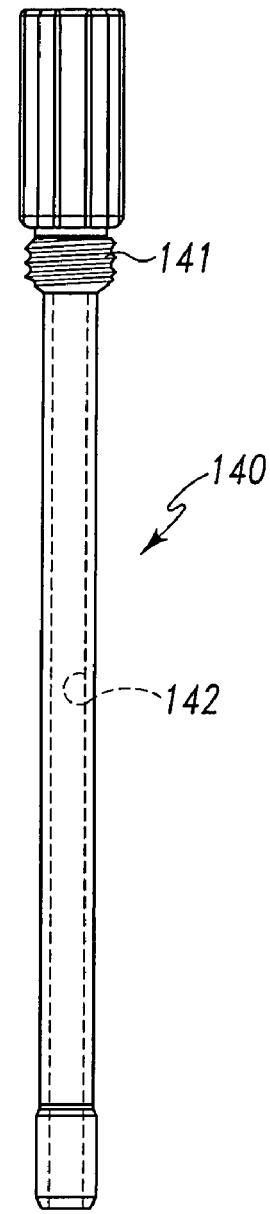
FIG. 43 is a side elevational view of the inner sheath of the drill guide assembly shown in FIG. 37.

Once the targeting component 120 is securely attached to the actuator 58, the holes 121 are utilized to facilitate accurate drilling of holes in the femur F in alignment with the screw holes of the side plate 6. A drill guide assembly 130 is used with the targeting component 120 for this purpose, and is shown in detail in FIGS. 36-43. The drill guide assembly 130 includes outer sheath 132 that is configured to be received in any of the plurality of holes 121 of the targeting component 120. FIG. 36 shows the outer sheath 132 extending through of the holes 121 of the targeting component 120. As is shown in FIG. 36, the handle assembly 54 is separated from the shaft 52 to allow ample space for manipulating the drill guide assembly 130 in relation to the targeting component 120. This is especially helpful when the drill guide assembly 130 is being used with the most proximal hole 121 of the targeting component 120. The outer sheath 132 defines a groove 137 on an outer surface thereof. A spring 150 is configured to extend circumferentially around the outer sheath 132 and be received in the groove 137. The spring 150 is shown in detail in FIG. 39. When the spring 150 is located within the groove 137 and the outer sheath 132 is positioned within one of the holes of the targeting component 120, the spring 150 assists in holding the outer sheath 132 in fixed relation to the targeting component 120. The drill guide assembly 130 further includes a handle shaft 134 attached to the outer sheath 132, and a handle 136 attached to the handle shaft 134. The outer sheath 132 defines a central passageway 133 extending therethrough. The outer sheath 132 includes a set of internal threads 135 located within the central passageway 133. The drill guide assembly 130 further includes a trocar 138 that is configured to extend through the central passageway 133. The trocar 138 is solid in cross section so that no passageway is defined therethrough. The trocar 138 has a set of external threads 139 configured to meshingly engage with the set of internal threads 135 so as to removably secure the trocar 138 to the outer sheath 132. The drill guide assembly 130 also includes an inner sheath 140 that is configured to extend through the central passageway 133. The inner sheath 140 defines a central passageway 142 extending therethrough. The inner sheath 140 also has a set of external threads 141 configured to meshingly engage with the set of internal threads 135 so as to removably secure the inner sheath 140 to the outer sheath 132. The inner sheath 140 is configured to allow for the passage of a drill (e.g. a 3.8 mm drill), while the outer sheath 132 is configured to allow for the passage of a hex driver (e.g. a 4.5 mm hex driver shank) therethrough.

Use of Instrumentation and Implant Components

Use of the instrumentation and implant components described above facilitate reduction of a hip fracture in a minimally invasive manner. In particular, in order to perform such a procedure, a patient P is placed supine on a standard fracture table. The fracture is then reduced and aligned using traction with external rotation followed by approximately 20 degrees of internal rotation to compress the fracture 13 (see FIG. 6). The reduction is then verified using dual-plane image intensification. The hip is thereafter prepared and draped in a conventional manner.

A guide pin 12 (e.g. a 3.2 mm guide pin) is exteriorly placed above the femoral neck to assess lateral positioning and neck angle. The tip of the guide pin is placed radiographically at the tip of the lesser trochanter of the femur F in the A/P plane with the pin extending laterally. A skin marker is used to place a line along this guide pin laterally. Next, the tip of the guide pin is radiographically placed at the apex of the femoral head, extending laterally and centrally down the femoral neck. A skin marker is again used to place a line along the guide pin extending to the posterior lateral aspect of the thigh. Then, the guide pin is placed longitudinally parallel to the lateral view of the femoral shaft and a line is created that intersects the point where the first two lines intersect. At the intersection of the three lines, a 3 to 5 cm incision I is made that extends distally. Thereafter, the dissection is carried sharply down through the skin and subcutaneous tissue to the fascia lata. The fascia lata is then split longitudinally, exposing the vastus lateralis to expose the lateral aspect of the femoral shaft. The skin may be retracted using retractors if desired.

The guide assembly 10 is then aligned such that the side 44 of the foot 28 or the side 46 of the foot 28 is facing upward and is visible, depending on the location of the fracture 13. This will ensure that the guide tube 16 of the guide assembly 10 is aligned to target the femoral head. To insert the guide assembly 10 into the incision I, the foot 28 of the guide assembly 10 is moved to its position shown in FIG. 5. Note that the foot 28 may further include a groove 154 that is aligned with the central axis of the guide assembly 10 which is similar in configuration to the groove 41 so that the foot 28 may be locked in fixed relation to the locking sleeve 32 in a manner similar to that discussed above with respect to locking the foot 28 at the position shown in FIG. 4. The foot 60 28 is inserted through the incision I until the tip of the foot 28 makes contact with the lateral aspect of the femur F. The locking nut 36 of the guide assembly 10 is then rotated until the foot 28 is free to pivot in relation to the locking sleeve 32. Under fluoroscopy, the foot 28 is slid distally along the lateral cortex of the femur F until the foot 28 is in a desired position. Then, the locking nut 36 is rotated in an opposite direction to that discussed above thereby causing the locking nut to urge the locking sleeve 32 distally to engage the tang 40 within the groove 41 of the foot 28. So positioned, the foot 28 is fixed in relation to the locking sleeve 32 at the position shown in FIG. 4.

The guide tube 16 should now be positioned relative to the femur F so that the guide tube will direct the guide pin 12 to lie at the highest angle necessary to position the pin next to the medial cortex and in the center of the femoral head in the anterior/posterior (A/P) plane. The guide pin 12 is then advanced through the guide tube 16 and the center of the femoral head in both the A/P and lateral planes to within 5 to 7 mm of the subchondral bone as is done.

After insertion of the guide pin 12 as discussed above, the locking nut 36 of the guide assembly 10 is rotated so as to free pivoting of the foot 28. Thereafter, the foot 28 of the guide assembly 10 is advanced out of the wound through the incision I.

Next, a reamer (not shown) is placed over the guide pin 12 and advanced through the incision I and into the proximal femur under image control as is done in a conventional procedure. Thereafter, a calibrated tap (not shown) is placed over the guide pin 12 and the neck and head of the femur F is tapped to within 5-7 mm of subchondral bone under image control.

Figure 44:
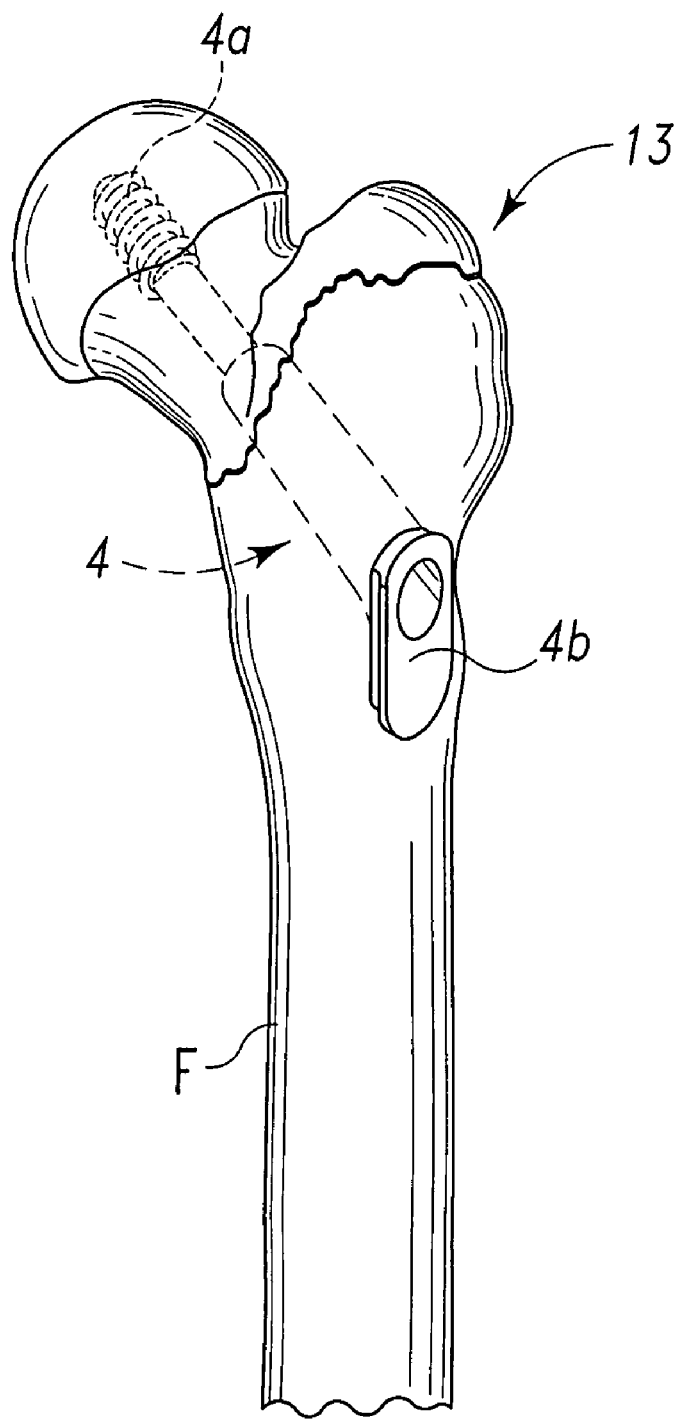
FIG. 44 is a perspective view of the captured screw assembly implanted in a femur according to the present disclosure, with the femur F and the capture screw assembly 2 shown removed from the body of the patient P for clarity of viewing.

In a conventional procedure, a surgeon would insert a captured screw assembly 4 and an associated side plate 6 into the wound at the same time. According to the minimal incision technique discussed herein, only the captured screw assembly 4 is inserted using standard techniques at this time. FIG. 7 shows the captured screw assembly 4 in the process of being implanted in the femur F over the guide pin 12. FIG. 44 shows the captured screw assembly 4 secured to the femur in accordance with the minimal incision technique. (Note that FIG. 44 shows the femur F and the captured screw assembly 4 removed from the body for clarity of viewing.) Once the captured screw assembly 4 has been secured within the femoral head and neck, the side plate 6 may be assembled to the barrel 4b. This is accomplished with the assistance of the plate holder assembly 50. A selected side plate 6 is pre-assembled to the plate holder assembly 50 through manipulation of the handle assembly 54 and the driver 62 as described above. Note that the handle assembly 54 and the driver 62 must both be rotated fully counter-clockwise to allow the side plate 6 to be advanced between the arms 76, 78 of the holder 56. Once the side plate 6 is positioned between the arms 76, 78, the driver 62 is advanced clockwise to close the arms 76, 78 onto the sides of the side plate 6, and then the handle assembly 54 is rotated clockwise until the side plate 6 is securely fastened in the distal part of the plate holder assembly 50. Note that the driver 62 may have a positive stop built into it that is reached to ensure that the plate is fully locked. Also, the handle assembly 54 is rotated until it can no longer advance. Next, verification is made that the distal screw holes of the side plate 6 are on the same side of the foot 60 as the impactor recess 96 defined in the foot 60. Proper orientation of the side plate 6 with respect to the foot 60 is shown in FIG. 10.

The plate holder assembly 50 is now manipulated to insert the side plate 6 through the incision I, and thereafter mate the side plate 6 with the barrel 4b of the captured screw assembly 4. In order to ensure full mating of the side plate 6 and the barrel 4b, the impactor 112 is manipulated until its distal end is received within the impactor recess 96 of the foot 60. Thereafter, the proximal end of the impactor is tapped firmly several times (e.g. three or four) to transmit force to the side plate 6 thereby ensuring the side plate 6 and the barrel 4b are fully mated.

After impaction, and while ensuring that the side plate 6 stays firmly mated to the barrel 4a inside the wound, the targeting component 120 is attached to the actuator 58 in the manner discussed above. In particular, the locking ring 64 is unthreaded from the set of external threads 102 on the locking ring 64 and then slid proximally. Then, the mating surface 122 of the targeting component 120 is mated with the polygonal-shaped surface 87 of the actuator 58. Then, verification occurs that the targeting component 120 extends parallel to the side plate 6 located inside the wound. Thereafter, the set of internal threads 108 of the locking ring 64 are meshingly engaged with the set of external threads of the driver 62 and tightened down. This causes the locking ring 64 to contact the targeting component 120 thereby securing the targeting component between the locking ring 64 and the clamping surface 89 of the actuator 58 (see FIG. 32).

With the targeting component 120 secured as shown in FIG. 32, the drill guide assembly 130 (with neither the trocar 138 nor the inner sheath 140 located within the central passageway 133 of the outer sheath 132) is then inserted into the most proximal hole 121 of the targeting component 120. As discussed above, the handle assembly 54 may be separated from the shaft 52 prior to this step. The drill guide assembly 130 is advanced until the distal end of the outer sheath 132 touches skin of the patient P. A mark is then made for a stab incision, and the skin is thereafter incised. The trocar 138 is then advanced into the central passageway 133 of the outer sheath 132 and thereafter its set of external threads 139 are mated with the set of internal threads 135 of the outer sheath 132. Now, the outer sheath is advanced until its distal tip contacts the side plate 6 in the most proximal hole 131. A shoulder 158 (see FIG. 38) defined on a proximal portion of the outer sheath 132 is in contact with a top surface of the targeting component 120 thereby indicating that it is fully seated. Thereafter, the trocar 138 is removed from the central passageway 133 of the outer sheath 132. The inner sheath 140 is now advanced into the central passageway 133 of the outer sheath 132 and thereafter its set of external threads 141 are mated with the set of internal threads 135 of the outer sheath 132. A drill (not shown) is advanced into the central passage 142 of the inner sheath 140 and is manipulated under fluoroscopy to drill both cortices of the femur F. The drill may be a 3.8 mm calibrated drill. The measurement on the drill is then noted when the tip of the drill protrudes from the medial cortex of the femur. A depth gauge device may also be used for this purpose. Thereafter, a power adaptor or a quick couple T-handle is then assembled to a 4.5 mm solid hex driver shank (as in a conventional technique). Then, the inner sheath 140 is removed from the outer sheath 132 and the 4.5 mm self-tapping screw 8 is driven through the outer sheath 132 and into the hole in the side plate 6 thereby securing the side plate 6 to the shaft of the femur F. The same procedure is repeated for placement of all of the screws 8 of the side plate 6.

After placement of the final distal screw 8, the targeting component 120 is detached from the actuator 58. Additional impaction with the impactor 112 (in a manner similar to the impaction described above) is performed, if desired. In particular, the impactor 112 may again be used to impact the side plate 6 into the barrel 4b with three to four firm taps on the strike cap 118 with a mallet.

After impaction, the plate holder assembly 50 is separated from the side plate 6 and removed from the wound. The side plate 6 is released by the plate holder assembly 50 by first turning the handle assembly 54 counter-clockwise until it is fully retracted. Then, the driver 62 is released, also by turning it counter-clockwise until fully retracted. These acts will cause the plate holder assembly 50 to release from the side plate 6. After such release, the plate holder assembly 50 is pulled out of the wound through the incision I in a direction perpendicular to the side plate 6. Slight anterior/posterior (A/P) movement of the plate holder assembly 50 may be necessary to fully disengage the plate holder assembly 50 from the side plate 6. Thereafter, the wound is closed in a conventional manner.

There is a plurality of advantages arising from the various features of each of the embodiments of the assembly described herein. It will be noted that alternative embodiments of the assembly may not include all of the features described yet still benefit from at least some of the advantages of such features. Those of ordinary skill in the art may readily devise their own implementations of the assembly that incorporates one or more of the features and fall within the spirit and scope of the present invention as defined by the appended claims.

What is claimed is:

1. An assembly, comprising:
    a holder having a first arm and a second arm, said holder being movable between a first configuration and a second configuration, and said holder defining a holder passageway
    an actuator movable in relation to said holder between a first position and a second position, wherein movement of said actuator from said first position to said second position causes movement of said holder from said first configuration to said second configuration;
    a bone plate having a plurality of fastener openings defined therein said bone plate being retained between said first arm and said second arm when said holder is positioned in said second configuration; and
    a press that is movable in relation to said holder,
    wherein said press includes (i) a bone plate contacting member positioned between said first arm and said second arm of said holder, and (ii) a shaft positioned within said holder passageway, said bone plate contacting member being secured to said shaft, and
    wherein said shaft is rotatable in relation to said bone plate contacting member when said bone plate contacting member is secured to said shaft.

2. The assembly of claim 1, wherein:
    said actuator includes a third arm and a fourth arm, and
    during movement of said actuator from said first position to said second position, (i) said third arm of said actuator contacts said first arm of said holder, and (ii) said fourth arm of said actuator contacts said second arm of said holder.

3. The assembly of claim 2, wherein both of said first arm and said second arm are positioned between said third arm and said fourth arm during movement of said actuator from said first position to said second position.

4. The assembly of claim 1, wherein:
    said actuator defines an actuator passageway, and
    a portion of said holder is located within said actuator passageway during movement of said actuator from said first position to said second position.

5. The assembly of claim 4, wherein said first arm and said second arm are both located outside of said actuator passageway during movement of said actuator from said first position to said second position.

6. The assembly of claim 1, wherein:
    said first arm of said holder includes a first projection,
    said second arm of said holder includes a second projection,
    said shaft is rotatable in relation to said holder, and
    rotation of said shaft in relation to said holder causes said bone plate to be clamped between said bone plate contacting member and said first and second projections.

7. The assembly of claim 6, wherein said shaft and said bone plate contacting member are configured such that said shaft rotates in relation to said bone plate contacting member when said shaft rotates in relation to said holder.

8. The assembly of claim 6, wherein:
    said holder includes a set of internal threads located within said holder passageway, and
    said shaft includes a set of external threads that are meshingly engaged with said internal threads during rotation of said shaft in relation to said holder.

9. The assembly of claim 1, further comprising a driver that is rotatable in relation to said holder, wherein:
    rotation of said driver in relation to said holder causes movement of said actuator from said first position to said second position.

10. The assembly of claim 9, wherein:
    said driver defines a driver passageway,
    said driver includes a set of internal threads located within said driver passageway, and
    said holder has a set of external threads that meshingly engage said set of internal threads during movement of said actuator from said first position to said second position.

11. The assembly of claim 10, wherein said actuator is interposed between said driver and said first and second arms of said holder during movement of said actuator from said first position to said second position.

12. The assembly of claim 9, further comprising a targeting component having a plurality of holes extending therethrough, wherein:
    said actuator defines a polygonal-shaped surface, and
    said targeting component has a mating surface that is configured to be at least partially complementary to said polygonal-shaped surface.

13. The assembly of claim 12, further comprising a locking member that is rotatably mounted on said driver, wherein:
    said actuator includes a clamping surface, and
    rotation of said locking member in relation to said driver causes clamping of said targeting component between said locking member and said clamping surface.

14. The assembly of claim 13, wherein:
    said locking member includes an internally threaded passage, and
    said driver includes an externally threaded portion configured to mate with said internally threaded passage.

15. The assembly of claim 12, further comprising a drill guide assembly extending through any one of said plurality of holes of said targeting component, wherein said drill guide assembly includes:
a first sheath configured to be received by any of said plurality of holes of said targeting component, said first sheath defining a first passageway, and
a handle attached to said first sheath,
wherein said drill guide assembly further includes a second sheath defining a second passageway said second sheath configured to be received in said first passageway of said first sheath.

16. The assembly of claim 1, further comprising an impactor spaced apart from said shaft, wherein:
said bone plate contacting member of said press has a recess defined therein, and
an end portion of said impactor is configured to be received in said recess.

17. The assembly of claim 1, further comprising a fastener, wherein:
said bone plate contacting member defines a press passageway extending therethough,
said shaft includes a reduced diameter end portion defining a shoulder,
said reduced diameter end portion is located within said press passageway,
said fastener is secured to said reduced diameter end portion, and
said bone plate contacting member is interposed between said shoulder and said fastener.

18. The assembly of claim 17, further comprising an impactor, wherein:
said bone plate contacting member of said press has a recess defined therein,
said recess is spaced apart from said press passageway, and
an end portion of said impactor is positioned within said recess.

19. An assembly, comprising:
a holder having a first arm and a second arm, said holder being movable between a first configuration and a second configuration, said holder defining a holder passageway; and
an actuator movable in relation to said holder between a first position and a second position,
wherein movement of said actuator from said first position to said second position causes movement of said holder from said first configuration to said second configuration,
wherein said first arm has a first bone plate contact portion,
wherein said second arm has a second bone plate contact portion,
wherein said first bone plate contact portion and said second bone plate contact portion are separated by a first distance when said holder is in said first configuration,
wherein said first bone plate contact portion and said second bone plate contact portion are separated by a second distance when said holder is in said second configuration, and
wherein said first distance is greater than said second distance,
further comprising a press that is movable in relation to said holder,
wherein said press includes (i) a bone plate contacting member positioned between said first arm and said second arm of said holder, and (ii) a shaft positioned within said holder said holder passageway, said bone plate contacting member being secured to said shaft, and
wherein said shaft is rotatable in relation to said bone plate contacting member when said bone plate contacting member is secured to said shaft.

20. The assembly of claim 19, wherein:
said actuator includes a third arm and a fourth arm, and
during movement of said actuator from said first position to said second position, (i) said third arm of said actuator is positioned in contact with said first arm of said holder, and (ii) said fourth arm of said actuator is positioned in contact with said second arm of said holder.

21. The assembly of claim 20, wherein both of said first arm and said second arm are positioned between said third arm and said fourth arm during movement of said actuator from said first position to said second position.

22. The assembly of claim 19, wherein:
said actuator defines an actuator passageway that is aligned with an axis of said actuator, and
a portion of said holder is located within said actuator passageway during movement of said actuator from said first position to said second position.

23. The assembly of claim 22, wherein said first and second arms are located outside of said actuator passageway during movement of said actuator from said first position to said second position.

24. The assembly of claim 19, wherein:
said first arm of said holder includes a first projection,
said second arm of said holder includes a second projection,
said shaft is rotatable in relation to said holder, and
rotation of said shaft in relation to said holder causes said bone plate contacting member to move toward said first and second projections.

25. The assembly of claim 24, wherein said shaft said shaft and said bone plate contacting member are configured such that said shaft rotates in relation to said bone plate contacting member when said shaft rotates in relation to said holder.

26. The assembly of claim 25, wherein:
said holder includes a set of internal threads located within said holder passageway, and
said shaft includes a set of external threads that are meshingly engaged with said internal threads during movement of said shaft in relation to said holder.

27. The assembly of claim 19, further comprising a driver that is rotatable in relation to said holder, wherein:
rotation of said driver in relation to said holder causes movement of said actuator from said first position to said second position.

28. The assembly of claim 27, wherein:
said driver defines a driver passageway,
said driver includes a set of internal threads located within said driver passageway, and
said holder has a set of external threads that meshingly engage said set of internal threads during movement of said actuator from said first position to said second position.

29. The assembly of claim 28, wherein said actuator is interposed between said driver and said first and second arms of said holder during movement of said actuator from said first position to said second position.

30. The assembly of claim 27, further comprising a targeting component having a plurality of openings extending therethrough, wherein:
said actuator defines a polygonal-shaped surface, and
said targeting component has a mating surface that is configured to be at least partially complementary to said polygonal-shaped surface.

31. The assembly of claim 30, further comprising a locking member that is rotatably attached to said driver, wherein:
said actuator includes a clamping surface, and
rotation of said locking member in relation to said driver causes clamping of said targeting component between said locking member and said clamping surface when said polygonal-shaped surface is mated with said mating surface,
said locking member includes an internally threaded passage, and
said driver includes an externally threaded portion configured to mate with said internally threaded passage.

32. The assembly of claim 30, further comprising a drill guide assembly positioned in any one of said plurality of openings of said targeting component, wherein said drill guide assembly includes:
a first sheath configured to be received by any of said plurality of openings of said targeting component, said first sheath defining a first passageway.

33. The assembly of claim 32, further comprising a second sheath defining a second passageway, said second sheath configured to be received in said first passageway of said first sheath.

34. The assembly of claim 19, further comprising an impactor spaced apart from said shaft, wherein:
said bone plate contacting member of said press has a recess defined therein, and
an end portion of said impactor is received in said recess.

35. The assembly of claim 19, further comprising a bone plate having a plurality of fastener openings defined therein, wherein:
said holder retains said bone plate between said first bone plate contact portion of said first arm and second bone plate contact portion of said second arm when said holder is positioned in said second configuration.

36. The assembly of claim 35, wherein:
when said holder is positioned in said second configuration, (i) said first bone plate contact portion of said first arm contacts said bone plate, and (ii) said second bone plate contact portion of said second arm contacts said bone plate.

37. The assembly of claim 19 further comprising a fastener, wherein:
said bone plate contacting member defines a press passageway extending therethough,
said shaft includes a reduced diameter end portion defining a shoulder,
said reduced diameter end portion is located within said press passageway,
said fastener is secured to said reduced diameter end portion, and
said bone plate contacting member is interposed between said shoulder and said fastener.

38. The assembly of claim 37, further comprising an impactor, wherein:
said bone plate contacting member of said press has a recess defined therein,
said recess is spaced apart from said press passageway, and
an end portion of said impactor is positioned within said recess.

* * * * *